(12) United States Patent
Everett et al.

(10) Patent No.: US 11,864,773 B2
(45) Date of Patent: Jan. 9, 2024

(54) DEVICE, SYSTEM AND METHOD FOR INTERMITTENT DISPLACEMENT OF BLOOD TO MITIGATE PERIPHERAL NERVE NEUROPATHY

(71) Applicant: Steve Eugene Everett, Kingsland, TX (US)

(72) Inventors: Jay Dean Everett, Austin, TX (US); Steve Eugene Everett, Kingsland, TX (US)

(73) Assignee: Steve Eugene Everett, Kingsland, TX (US)

( * ) Notice: Subject to any disclaimer, the term of this patent is extended or adjusted under 35 U.S.C. 154(b) by 955 days.

(21) Appl. No.: 16/834,807

(22) Filed: Mar. 30, 2020

(65) Prior Publication Data

US 2020/0222059 A1 Jul. 16, 2020

Related U.S. Application Data

(62) Division of application No. 16/695,114, filed on Nov. 25, 2019, now Pat. No. 10,646,233.
(Continued)

(51) Int. Cl.
*A61B 17/135* (2006.01)
*A61H 9/00* (2006.01)
*A61H 33/14* (2006.01)

(52) U.S. Cl.
CPC ....... *A61B 17/1355* (2013.01); *A61H 9/0007* (2013.01); *A61H 9/0092* (2013.01); *A61H 2033/143* (2013.01)

(58) Field of Classification Search
CPC .............. A61B 17/1355; A61B 17/132; A61B 17/1322; A61B 17/135; A61H 9/0007;
(Continued)

(56) References Cited

U.S. PATENT DOCUMENTS 2,113,253 A 12/1935 Gray
3,403,673 A 7/1965 MacLeod
(Continued)

FOREIGN PATENT DOCUMENTS

CN 105832522 A 8/2016
CN 208838305 5/2019
(Continued)

*Primary Examiner* — Sarah Al Hashimi
*Assistant Examiner* — Hans Kaliher
(74) *Attorney, Agent, or Firm* — David O. Simmons; IVC Patent Agency

(57) ABSTRACT

Embodiments of the present invention are directed to devices, systems and methods adapted for implementing intermittent displacement of blood to mitigate peripheral nerve neuropathy such as that induced by chemotherapeutic agents (i.e., chemotherapy-induced neuropathy (CIN)) that are administered to a patient. Such devices, systems and methods advantageously provide for precise, uniform and controlled blood flow occluding (and optionally blood displacing) compression along irregular surfaces of an appendage of a patient. Such precise, uniform and controlled blood occluding compression is imparted upon the epidermal and dermis skin layers within the aforementioned areas of a patient's extremities to decrease the time that free nerve endings located in the epidermal and encapsulated nerve endings located in the dermis skin layers are exposed to nerve damaging chemotherapy chemicals, thereby substantially decreasing CIN caused by prolonged exposure to such chemicals.

31 Claims, 8 Drawing Sheets

Related U.S. Application Data

(60) Provisional application No. 62/857,454, filed on Jun. 5, 2019, provisional application No. 62/790,473, filed on Jan. 10, 2019, provisional application No. 62/781,516, filed on Dec. 18, 2018, provisional application No. 62/772,097, filed on Nov. 28, 2018.

(58) Field of Classification Search
CPC ............... A61H 9/0092; A61H 9/0071; A61H 2033/143; A61H 2205/106; A61M 35/10; A61M 35/30; A61M 35/00; A61M 2202/0208; A61G 10/026
See application file for complete search history.

(56) References Cited

U.S. PATENT DOCUMENTS

| | | | |
|---|---|---|---|
| 3,896,794 | A | 7/1975 | McGrath |
| 4,206,751 | A | 6/1980 | Scheider |
| 4,624,244 | A | 11/1986 | Taheri |
| 4,781,189 | A | 11/1988 | Vijil-Rosales |
| 6,921,373 | B1 | 7/2005 | Bernstein |
| 7,896,823 | B2 | 3/2011 | Mangrum et al. |
| 7,959,588 | B1 | 6/2011 | Wolpa |
| 9,615,991 | B2 | 4/2017 | Logan et al. |
| 2009/0177184 | A1 | 7/2009 | Christensen et al. |
| 2010/0105993 | A1 | 4/2010 | Naghavi et al. |
| 2010/0324611 | A1* | 12/2010 | Deming ................ A43B 7/147 607/2 |
| 2012/0172774 | A1 | 7/2012 | Lowe et al. |
| 2013/0012847 | A1 | 1/2013 | Lowe et al. |
| 2014/0046411 | A1 | 2/2014 | Elkins et al. |
| 2014/0066786 | A1* | 3/2014 | Naghavi ............ A61B 17/1355 600/481 |
| 2015/0351957 | A1 | 12/2015 | Wilder-Smith et al. |
| 2016/0338873 | A1 | 11/2016 | Parish et al. |
| 2018/0177737 | A1* | 6/2018 | Yaniv ................ B01F 23/2323 |
| 2018/0199879 | A1 | 7/2018 | Kanistros |
| 2019/0099322 | A1 | 4/2019 | ElderSteirn et al. |

FOREIGN PATENT DOCUMENTS

| | | | |
|---|---|---|---|
| MX | 2010014309 A | * | 12/2010 |
| WO | 2007010278 | | 1/2007 |
| WO | 2021155030 | | 5/2021 |
| WO | 2022090346 | | 5/2022 |
| WO | 2022098308 | | 12/2022 |

* cited by examiner

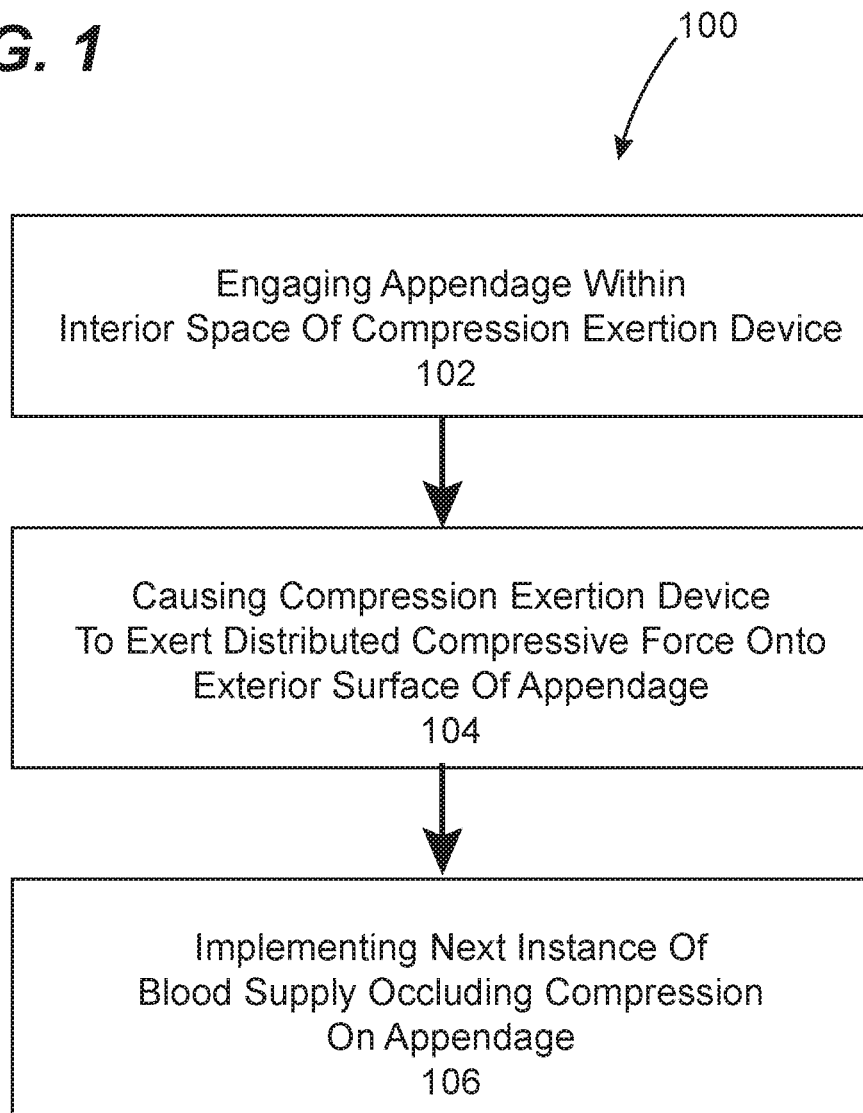

DEVICE, SYSTEM AND METHOD FOR INTERMITTENT DISPLACEMENT OF BLOOD TO MITIGATE PERIPHERAL NERVE NEUROPATHY

CROSS-REFERENCE TO RELATED APPLICATIONS

This divisional patent application claims priority from co-pending United States Non-provisional Patent Application having Ser. No. 16/695,114, filed 25 Nov. 2019, entitled "Device, System and Method For Intermittent Displacement of Blood to Mitigate Peripheral Nerve Neuropathy", having a common applicant herewith and being incorporated herein in its entirety by reference.

United States Non-provisional Patent Application having Ser. No. 16/695,114 claims priority from United States Provisional Patent Application having Ser. No. 62/772,097, filed 28 Nov. 2018, entitled "Peripheral Nerve Neuropathy Prevention by Intermittent Blood Displacement", having a common applicant herewith and being incorporated herein in its entirety by reference.

United States Non-provisional Patent Application having Ser. No. 16/695,114 claims priority from United States Provisional Patent Application having Ser. No. 62/781,516, filed 18 Dec. 2018, entitled "Peripheral Nerve Neuropathy Prevention by Intermittent Blood Displacement", having a common applicant herewith and being incorporated herein in its entirety by reference.

United States Non-provisional Patent Application having Ser. No. 16/695,114 claims priority from United States Provisional Patent Application having Ser. No. 62/790,473, filed 10 Jan. 2019, entitled "Peripheral Nerve Neuropathy Prevention by Intermittent Blood Displacement", having a common applicant herewith and being incorporated herein in its entirety by reference.

United States Non-provisional Patent Application having Ser. No. 16/695,114 claims priority from United States Provisional Patent Application having Ser. No. 62/857,454, filed 5 Jun. 2019, entitled "Peripheral Nerve Neuropathy Prevention", having a common applicant herewith and being incorporated herein in its entirety by reference.

FIELD OF THE DISCLOSURE

The disclosures made herein relate generally to treatment of cancer patients, more particularly, to devices, systems and methods for intermittent displacement of blood to mitigate peripheral nerve neuropathy.

BACKGROUND

Peripheral neuropathy is a condition that affects nerves outside of the brain and spinal cord (i.e., peripheral nerves). Peripheral neuropathy is often exhibited in patient's hands and feet due to the vast amount of nerves within such appendages. Peripheral neuropathy is known to affect both free nerves endings within the epidermal skin layer (i.e., unencapsulated nerves endings) and the nerve endings within the dermis skin layer (i.e., encapsulated nerves endings). Ailments in a portion of the body exhibiting peripheral neuropathy include, but are not limited to, weakness, numbness and pain.

Peripheral neuropathy is known to be caused by a genetic condition or by one or more of many acquired conditions. One such acquired condition that is of particular interest is peripheral neuropathy resulting from treatment of cancer with one or more cytotoxic drugs causing the death of healthy and malignant cells (i.e., commonly referred to as chemotherapy). In this manner, chemotherapy treatment of cancer thus is known to cause chemotherapy-induced neuropathy (CIN)). CIN is severe side effect which occurs in a high majority of cancer patients after treatment with chemotherapeutics. Symptoms of peripheral neuropathy are usually mild to begin with and gradually worsen affecting frequently the hands, feet and lower legs. The soles of the feet and palms of the hands are most susceptible due to a high concentration of nerve endings (e.g., as many as 200,000 nerve endings per sole).

Several chemotherapeutic agents are known to cause peripheral neuropathy. Examples of these chemotherapeutic agents include, but are not limited to, vincristine and vinca alkaloids, platinum compounds (e.g., cisplatin, oxaliplatin, carboplatin, taxanes, epothilones, bortezomib), thalidomide and the like. Although the exact mode of action in which these drugs cause nerve damage is not well known, it is thought that the general mode of action disruption or alteration is signal flow within nerve cells. For example, platinum compounds such as oxaliplatin are thought to accumulate in the dorsal root ganglia and produce hyperexcitability, whereas vinca alkaloids induce alterations in the cellular micro-tubuli structure leading to disruption of the axonal flow. The neurotoxicity of these agents is type and dose dependent, and severity of neuropathy is generally increasing with duration of treatment. CIN is known to be potentially irreversible. Chemotherapeutic agents are administered for a prescribed duration of time and/or quantity of the agent (i.e., an amount of delivery).

Currently, there are no effective treatment methods available to prevent or cure CIN. Although some neuroprotective agents are thought to decrease the neurotoxicity of the chemotherapeutic agent, there is no concrete clinical evidence supporting this data and the compounds to prevent CIN are known to cause side effects as well. For example, Omega-3 fatty acids are thought to have neuroprotective function in peripheral neuropathy induced by Paclitaxel in breast cancer patients, but these results have yet to be confirmed. As there are no known curative treatment options known for CIN sufferers and the use of chemotherapeutics is often unavoidable for many cancer patients, prevention is a much more viable option than curative.

A recent attempt at prevention of CIN has been tried through induced hypothermia using frozen gloves and socks. In such hypothermia treatment of CIN, as disclosed in United Stated Patent Application Publication no. 20150351957A1, the temperature of the foot and lower leg of a patient was lowered, thereby producing slowed or restricted blood flow. This slowed or restricted blood flow is disclosed as reducing exposure to the harmful chemotherapeutic agents. However, with such hypothermia treatment, there is still blood circulation such that chemotherapeutic agent exposure is only mildly limited. Another problem with this hypothermia treatment approach is the discomfort of hypothermia on the patient for extended periods of time.

Compression therapy uses compression to intermittently displaced blood for enhancing blood circulation, diminishing post-operative pain and swelling, reducing wound healing time, and aiding in the treatment and healing of stasis dermatitis, venous stasis ulcers, arterial and diabetic leg ulcers, chronic venous insufficiency and reduction of edema in the lower limbs. Although compression therapy does provide intermittent displacement of blood, the intermittent displacement of blood by application of pressure does not displace and limit blood supply to nerve endings to limit exposure to nerve endings from harmful chemicals. Rather, it is intended to promote blood movement and circulation by allowing blood to return to a treatment area and then to repeat the cycle frequently in a pulsing manner to artificially cause the movement of blood. In this respect, compression therapy does not limit the exposure time of peripheral nerve endings to the chemically contaminated blood supply. Compression therapy does not provide for the decrease in time nerve endings located in the dermis skin layers are exposed to nerve damaging chemotherapy agents to thereby decrease nerve damage caused by prolonged exposure to chemotherapeutic agents. As such, the functionality of compression therapy differs greatly from the intermittent displacement of blood from the dermis skin layers and the simultaneous occlusion of capillary blood vessels supplying blood to selected dermis skin areas and to the nerve endings within the epidermal and dermis skin layer.

Therefore, a CIN treatment approach that provides for a more limited exposure of the chemotherapeutic agents to peripheral nerve ending to substantially increasing the success of the prevention of CIN in a manner that overcomes drawbacks associated with conventional CIN treatment approaches would be advantageous, desirable and useful.

SUMMARY OF THE DISCLOSURE

Embodiments of the present invention are directed to devices, systems and methods adapted for implementing intermittent displacement of blood to mitigate peripheral nerve neuropathy such as that induced by chemotherapeutic agents (i.e., chemotherapy-induced neuropathy (CIN)) that are administered to a patient over a prescribed amount of delivery (e.g., time for which a flow of chemotherapeutic agent is delivered and/or volume of chemotherapeutic agent delivered). More specifically, embodiments of the present invention advantageously provide for precise, uniform and controlled blood flow occluding (and optionally blood displacing) compression along irregular surfaces of a human's hands and feet, including the spaces between the toes and fingers, the entire sole, sides of the soles, heals and toes of the foot and entire palm, fingers and palm sides of the hand. Such precise, uniform and controlled blood occluding compression (e.g., at least partially occluding blood flow) is imparted upon the epidermal and dermis skin layers within the aforementioned areas of a patient's extremities to decrease the time that free nerve endings located in the epidermal and encapsulated nerve endings located in the dermis skin layers are exposed to nerve damaging chemotherapy chemicals, thereby substantially decreasing CIN caused by prolonged exposure to such chemicals. To further limit CIN, in combination with the aforementioned controlled blood-occluding compression, embodiments of the present invention can be adapted to simultaneously provide bio-available-oxygen through the epidermal skin to the peripheral nerve endings, the bio-available oxygen is carried through the epidermal skin into the dermis layer within and aqueous pressure distribution medium. In this regard, embodiments of the present invention cause distributed compression that displaces and at least partially occludes the blood supply to the dermis and epidermal skin layer that are highly susceptible to the damage caused by chemotherapeutic agents while actively mitigating tissue damage resulting from blood-occluding compression thereof.

In one or more embodiments other embodiments of the present invention, a method for mitigating peripheral nerve neuropathy associated with chemotherapy treatment comprises administering a chemotherapeutic agent to a patient and exerting a compressive pressure on an appendage of the patient. The chemotherapeutic agent is administered for a prescribed amount of delivery. Exerting the compressive pressure on the appendage of the patient is performed during the administering of at least a portion of the prescribed amount of delivery. The compressive pressure is exerted for causing at least one of a magnitude of the compressive pressure and a duration of time for the compressive pressure being exerted to at least partially occlude blood flow into epidermal tissue of the appendage.

In one or more embodiments other embodiments of the present invention, a system for mitigating peripheral nerve neuropathy associated with chemotherapy treatment comprises a compression exertion device having an interior space adapted for receiving an appendage of a patient and a pressure controller operably attached to the compression exertion device to cause a compression-inducing medium within the compression exertion device to exert compressive pressure on the appendage during at least a portion of a prescribed amount of delivery of a chemotherapeutic agent to the patient. The compression exertion device includes a sealing component engageable with at least one of a portion of the appendage and a limb to which the appendage is attached when the appendage is positioned within the interior space. The pressure controller being operably attached to the compression exertion device to cause the compression-inducing medium within the compression exertion device to exert compressive pressure on the appendage includes causing at least one of a magnitude of the compressive pressure and a duration of time for the compressive pressure being exerted to at least partially occlude blood flow into epidermal tissue of the appendage. The pressure controller monitors administration of a chemotherapeutic agent to a patient to enable the compressive pressure to be provided as a function of the administration of the chemotherapeutic agent to the patient during a prescribed amount of delivery thereof.

In one or more embodiments other embodiments of the present invention, a compression exertion device is adapted for use with a peripheral nerve neuropathy system during chemotherapy treatment. The peripheral nerve neuropathy system is operably attachable to the pressure controller to enable pressurization of the compression exertion device for causing compressive pressure to be exerted by the compression exertion device on an appendage of a patient. A pressure controller of the peripheral nerve neuropathy system monitors administration of a chemotherapeutic agent to a patient to enable the compressive pressure to be provided as a function of the administration of the chemotherapeutic agent to the patient during a prescribed amount of delivery thereof. The compression exertion device comprises a compression body, a sealing component, an expansion cavity and in at least one or more embodiments a quantity of an aqueous compression inducing medium component capable of carrying bio-available oxygen through the epidermal skin layer into the dermis skin layer. The compression body including an interior space adapted for having the appendage of the patient engaged therein. The interior space encompasses at least a portion of an exterior surface of the appendage. The sealing component is engageable with at least one of a portion of the appendage and a limb to which the appendage is attached when the appendage is positioned within the interior space. The expansion cavity has a wall thereof defining at least a portion of the interior space. The aqueous bio-available oxygen pressure distribution medium component can comprise nano oxygen bubbles, water, at least one penetration enhancer.

In one or more embodiments, the compression exertion device and parts thereof can be made from a variety of man-made or natural rubbers, plastics and the like, having a hardness on the harness scale 00 of from between 10 to 90 and resistance to expansion from between about 10 mm hg and 155 mm hg.

In one or more embodiments, the compression exertion device may comprise a membrane for passage of oxygen while other parts may comprise woven non-woven textile resistant to expansion.

In one or more embodiments, a component of the compression exertion device comprises an aqueous bio-available oxygen pressure distribution medium comprised of a water solution, comprising nano oxygen bubbles (preferably smaller than 200 nm), a water solution comprising a mixture of at least one or more of skin penetration enhancers including water, urea, glycol, ethanol, taurine to name a few and nano oxygen bubbles therein said pressure distribution medium providing thereby a safe epidermal penetrating aqueous oxygen carrier providing diffusion of oxygen into the epidermal skin layer and into the dermis skin layer and tissues therein, an oxygen charged perfluorocarbon composition.

In one or more embodiments, the pressure distribution medium is pressurized from between about 10 mm hg and 50 mm hg and is in intimate contact with the epidermal skin layer for the duration of the chemo therapy treatment without a cyclical operation.

In one or more embodiments, the aqueous pressure distribution medium is pressurized from between about 10 mm hg and 50 mm hg and is in intimate contact with the epidermal skin layer for the duration of the chemotherapy treatment without a cyclical operation.

In one or more embodiments of the present invention, exerting the compressive pressure is initiated prior to the administering of the chemotherapeutic agent and administering the chemotherapeutic agent is initiated after blood flow into at least a portion the dermis tissue of the appendage is at least partially occluded.

In one or more embodiments of the present invention, the compressive pressure is released after the administering of the chemotherapeutic agent is initiated and the compressive pressure is reapplied after blood flow is resumed through the appendage for a designated duration of time.

In one or more embodiments of the present invention, exerting the compressive pressure on the appendage includes pressurizing a compression-inducing medium surrounding the appendage.

In one or more embodiments of the present invention, exerting the compressive pressure on the appendage includes positioning the appendage within an interior space of a compression exertion device and delivering a compression-inducing medium into at least one of the interior space of the compression exertion device and an expansion cavity of the compression exertion device.

In one or more embodiments of the present invention, delivering the compression-inducing medium includes delivering the compression-inducing medium into the interior space of the compression exertion device and the compression-inducing medium is an oxygen-carrying medium capable of diffusing oxygen into epidermal tissue of the appendage.

These and other objects, embodiments, advantages and/or distinctions of the present invention will become readily apparent upon further review of the following specification, associated drawings and appended claims.

BRIEF DESCRIPTION OF THE DRAWINGS

FIG. 1 is a flow diagram view showing a perspective view showing a method in accordance with an embodiment of the present invention for blood supply occluding compression of a treated appendage of a patient to mitigate chemotherapy-induced neuropathy within a treated appendage.

DETAILED DESCRIPTION

Figure 4:
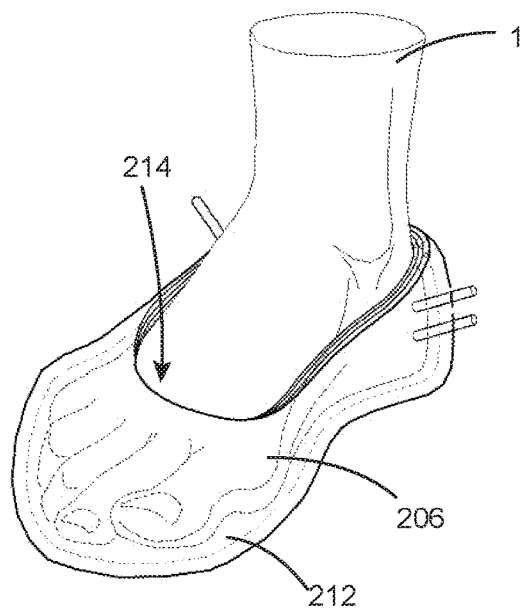
FIG. 4 is an illustrative view showing a compression body of the compression exertion device of FIG. 3.

Devices, methods and systems configured in accordance with one or more embodiments of the present invention are adapted to achieve intermittent blood flow occlusion and optional displacement of blood within an appendage of a patient (i.e., the treated appendage) to mitigate peripheral nerve neuropathy. Peripheral nerve neuropathy can be induced by chemotherapeutic agents (i.e., chemotherapy-induced neuropathy (CIN)). Advantageously, such devices, methods and systems provide for precise, uniform and controlled compression of the treated appendage. The objective of such treatment is to decreases the time that free nerve endings located in the epidermal and encapsulated nerve endings located in the dermis skin layers are exposed to nerve damaging chemotherapy chemicals, thereby substantially decreasing CIN caused by prolonged exposure to such chemicals. To this end, devices, methods and systems configured in accordance with one or more embodiments of the present invention provide distributed (e.g., uniform) compression of an appendage to at least partially occlude (i.e., inhibit) the supply of blood to the dermis skin layer that are highly susceptible to the damage caused by chemotherapeutic agents while actively mitigating tissue damage resulting from the blood supply occluding compression. Partial blood flow occlusion can be such that a suitable degree of blood flow is maintained such as to provide the required amount of blood flow for retaining cell life (e.g., blood flow of about 5% or less, 10% or less, 25% or less about 5-10%, about 10-25%, less than about 25%, less than about 50%). This blood supply occluding compression can also be of sufficient magnitude or duration to cause displacement of blood from within the dermis skin layers of the treated appendage.

Underlying objectives of the methods for intermittent displacement of blood within a treated appendage of a patient to mitigate CIN within a treated appendage in accordance with embodiments of the present invention (e.g., the method 100 disclosed below) include both providing distributed compression of an appendage to at least partially occlude (i.e., inhibit) the supply of blood to the dermis skin layer that are highly susceptible to the damage caused by chemotherapeutic agents and actively mitigating tissue damage resulting from the blood supply occluding compression. Both of these underlying objectives are related to sensory nerves located in the epidermal skin layer, which are also referred to as fee nerve endings. When free nerve endings are not functioning properly, they produce symptoms such as numbness, pins and needles, pain, tingling and burning, which are the symptoms accompanied with CIN. Although the epidermal skin layer does not have blood supply, it is nevertheless highly blood oxygen thirsty. These free or unencapsulated nerve ending extend from the border between the dermis and the epidermal skin layer up and into the epidermal skin layer. This being the case, it is believed that the area of joining between the dermis and the epidermal is where damage is caused by chemotherapeutic agents. The free nerve endings are not encapsulated as other peripheral nerves are and are much more susceptible to damage from the chemotherapeutic agents.

Immediately below the epidermis is the papillary dermis and papillary plexus and the superficial arteriovenous plexus (capillary bed). The papillary dermis tissue is where blood from the capillary arteries enters and gaseous exchanges take place supplying oxygen to the peripheral nerve endings. Additionally, blood in the papillary dermis tissue can scavenge for toxins and carry the toxins to other organs for removal. Blood exits the arterial capillaries at about 35 mm hg and into the surrounding tissue, the pressure in this surrounding tissue is about 25 mm hg. Blood from the surrounding tissue reenters the venous capillaries because, at that point, the hydrostatic pressure in the veins is about 18 mm hg while the pressure in the surrounding tissue is about 25 mm hg. The surrounding tissue where this blood, gas and toxin exchange takes place is where it is believed that the chemo toxins can build up and seep in alongside the free nerve endings within the epidermis skin layer and cause the damage to the very delicate nerve ending in this area.

To minimize chemo toxic blood (i.e., blood containing chemotherapeutic agents) in contact with the fragile nerve ending and provide a supply of oxygen simultaneously to the tissues and nerve endings, implements in accordance with embodiments of the present invention (e.g., devices, systems and methods) provide for uniform compression of the tissues surrounding the nerve endings. The pressure applied to the surrounding tissue to prevent mechanical or other damage to the nerve ending should be at or below the arterial capillary pressure of 35 mm hg. Two things happen when pressure is applied: first, any blood containing chemotherapeutic agents is displaced through the venous wall and is returned to other organs for removal and, second, the pressure being intermittently supplied equals the pressure in the capillary arteries of 35 mm hg. This will prevent further ingress of chemo blood toxins into the surrounding issue. In response to the pressure being intermittently released, blood containing chemotherapeutic agents will fill into the surrounding tissue for oxygenation of the tissues and nerve endings. As pressure is applied and blood is displaced in the tissue, the majority of chemotherapeutic agents will pass with the blood into the venous capillaries and the cycles continue as necessary.

Referring to FIG. 1, a method 100 for blood supply occluding compression of a treated appendage of a patient to mitigate CIN within a treated appendage. To this end, the method 100 provides for precise, uniform and controlled blood supply occluding compression of the epidermal and dermis skin layers of the treated appendage. This precise, uniform and controlled blood supply occluding compression inhibits the supply of blood to the dermal layers that are highly susceptible to the damage caused by chemotherapeutic agents. The method 100 is adapted to provide such exerted blood supply occluding compression in a manner that limits tissue damage resulting from the exerted blood supply occluding compression, thereby substantially decreasing CIN caused by prolonged exposure of nerves of the treated appendage to chemotherapeutic agents. The blood supply occluding compression can be of sufficient magnitude and/or duration so as to at least partially occlude blood flow into the appendage and to displace blood from within at least a portion of the dermis skin layer of the appendage.

The method 100 begins with an operation 102 of engaging an appendage within an interior space of a compression exertion device being performed. The operation 102 is performed in conjunction with (e.g., prior to or contemporaneously with) initiation of a chemotherapy treatment session of the patient. For example, one or both feet and/or hands of the patient can be placed within an interior space of one of more compression exertion devices. As discussed below, the compression exertion device(s) is(are) adapted for enabling a gaseous and/or fluid compression inducing medium to impart a distributed and uniform compressive force onto an exterior surface of the appendage(s).

Prior to or in combination with engaging an appendage within an interior space of a compression exertion device, an outermost protective skin layer of the appendage (generally referred to as the Stratum Corium) is modified for promoting transfer of gaseous and/or liquid material therethrough. Examples of such Stratum Corium modification include, but are not limited to, pre-soaking the treated area of appendage in an aqueous solution of water comprising one or more penetration enhancers, microscopic, nano sized oxygen bubbles, for a period of time to increase the oxygen levels within the epidermal skin layer and to saturate the epidermal layer with oxygenated water prior to commencement of treatment. Adhesive tape stripping, micro-punctures, micro dermal abrasions, chemical peels and the like are other pre-treatments to the stratum corium. The stratum corium comprises between 5-10% water but can be saturated up to 40% or more water. Diffusion of gases through the skin has been shown in multiple studies to increase exponentially with increased water content of the stratum corium, increasing the diffusion rate of gases 2-fold to 4-fold when wet. Modification therefore of the stratum corium for promoting transfer of gaseous and/or liquid material therethrough is beneficial to enable an oxygen enriched flowable medium that delivers oxygen into the dermis skin layer providing oxygen to be received by nerve endings and other cellular mater within the appendage. As discussed below in greater detail, such oxygen delivery limits oxygen-deprived necrosis (i.e., tissue damage) resulting from blood supply occluding compression of the method 100.

After the appendage is placed within the compression exertion device and in combination with chemotherapy treatment, an operation 104 of causing the compression exertion device to exert a distributed compressive force onto an exterior surface of the appendage is performed for providing a current instance of blood supply occluding compression on the appendage. To this end, in one or more embodiments of the present invention, a gaseous and/or fluid compression-inducing medium can be delivered to compression exertion device and such compression-inducing medium either directly or indirectly causing a generally uniform compressive force to be exerted onto an exterior surface of the appendage that is located within the interior space of the compression exertion device. The compression-inducing medium may be an oxygen carrying medium, as discussed below in greater detail.

In one or more preferred embodiments, the current instance of blood supply occluding compression pressure is induced for a period, for example 1 minute, before administration of chemotherapy. Preferably, but not necessarily, the blood supply occluding compression of the appendage is of a sufficient magnitude to also cause partial displacement of blood from within the dermis skin layer of the appendage. For example, the compression-inducing medium can be maintained at an applied pressure preferably of between about 10 mm hg to about 25 mm hg and more preferred from between about 25 mm hg to about 50 mm hg. Displacement of blood from within the appendage advantageously limits exposure of nerve tissue (and skin tissue in general) to blood containing chemotherapeutic agents, thereby advantageously mitigating CIN within the appendage.

In one or more embodiments, exerting the distributed compressive force onto the exterior surface of the appendage can include delivering oxygen (e.g., dissolved oxygen in thermally conditioned water) to skin tissue of the appendage. Delivering oxygen to the skin tissue serves to maintain life of skin tissue cells during the blood supply occluding compression and possible displacement of blood from within the dermis skin layer of the appendage, thus limiting oxygen-deprived necrosis. To this end, oxygen delivery can be provided for by diffusion (i.e., transfer) of oxygen via an oxygen enriched flowable medium such as a fluid (e.g., a gas of a liquid), a gel, a cream, a serum, a paste or a combination thereof. The oxygen enriched flowable medium can be an oxygen carrier that can include one or more penetration enhancers such as those generally regarded as safe by the FDA (e.g., vitamin E, transcutol, oleic acid, glycols, ethanol, terpines, menthols, 1,8-cineole d-limolene phospholipids and water), one or more perfluorocarbons (e.g., perfluorohexane, perfluoroperhydrophenanthrene perfluorodecalin, fiflow perfluorocarbon products) one or more pharmaceutical grade emulsifier, surfactants and the like. The oxygen enriched flowable medium facilitates oxygen diffusion into and through the stratum corium of the patient's skin into the dermis skin layer, thereby facilitating diffusion of oxygen supply to peripheral nerve endings and skin tissue during the blood supply occluding compression.

In some embodiments, oxygen diffusion can be via direct contact of the oxygen enriched flowable medium with the patient's skin, such as by the oxygen enriched flowable medium being pressurized to cause the blood supply occluding compression within the compression exertion device and being in direct contact with the appendage. In other embodiments, oxygen diffusion can be via indirect contact of the oxygen enriched flowable medium with the patient's skin, such as by the oxygen enriched flowable medium being subjected to exerted pressure that causes the blood supply occluding compression within the compression exertion device and separated from a surface of the appendage by a membrane through which oxygen can pass. In yet other embodiments, oxygen diffusion can be via direct contact of the oxygen enriched flowable medium with the patient's skin, but where the oxygen enriched flowable medium is in indirect contact with a compressive force inducing fluid within the compression exertion device. Flowability of the oxygen enriched flowable medium under pressure enables the oxygen enriched flowable medium to be self-contouring in regard to a contour of the exterior surface of the appendage, which serves to promote equally distributed blood supply occluding compression and oxygen diffusion into and through the stratum corium of the patient's skin.

Water including dissolved oxygen has been shown to substantially supply oxygen into the epidermis up to 700 microns deep when soaking feet in oxygenated water. With the edition of one or more water compatible and generally excepted as safe (e.g., by the FDA standard(s)) skin penetration enhancers, oxygen is able to penetrate the epidermal and into the dermis skin layer and tissues, allowing oxygen to be supplied to tissues and nerves during blood supply occluding compression. An important aspect of a compression-inducing medium utilized with implements in accordance with embodiments of the present invention can be its oxygen carrying capacity of some components such as water, fluorocarbons with excellent gas exchanging capacity oxygen and carbon dioxide. This oxygen carrying capacity makes compression-inducing medium comprising these components an ideal aqueous pressure distribution medium.

In one or more embodiments, the blood supply occluding compression can be imparted through a quantity (e.g., pre-determined quantity) of flowable medium such as, for example, an aqueous bio-available oxygen in a liquid medium that is applied to the appendage prior to or as a result of being engaged within the interior space of the compression exertion device. The quantity of flowable medium can be a metered quantity of aqueous medium that is determined based upon at least one of a volume of the interior space of the compression exertion device, a size of the patient's appendage, an efficiency by which oxygen is capable of being transferred into the patient's appendage, a diffusion rate enabled by a membrane through which the oxygen is diffused, or combination thereof.

During a current instance of the distributed compressive force being exerted onto the exterior surface of the appendage, an operation 106 of implementing a next instance of blood supply occluding compression on the appendage, where such next instance now become the current instance. To this end, implementing the next instance of blood supply occluding compression can include monitoring of a pressure exerted on the appendage by the compression-inducing medium and thereafter controlling such pressure to terminate the blood supply occluding compression for a designated period of time and then re-apply pressure for causing blood supply occluding compression. In this manner, after a prescribed period of time and/or after a level of blood oxygen in the appendage decreases to a prescribed level, pressure exerted on the appendage via the compression-inducing medium can be reduced or eliminated for a prescribed period or time to allow blood flow to the appendage and then pressure exerted on the appendage via the compression-inducing medium can be re-applied. To prevent oxygen deprived tissue necrosis, this intermittent application of pressure can be repeatedly carried out throughout the administration of chemotherapy treatment at uniform (e.g., solely time-based) or non-uniform intervals (e.g., at least partially blood oxygen-level based). In a specific implementation of such intermittent pressure application, blood supply occluding compression is maintained for a period preferably of from about 3 minutes to about 10 minutes and still more preferred from about 10 minutes to about 30 minutes and still more preferably from between about 30 minutes to and about 60 minutes and still more preferably from about 60 minutes to about 90 minutes after initiation of a current instance of blood supply occluding compression.

As disclosed above, exerting the distributed compressive force onto the exterior surface of the appendage can include delivering oxygen via dissolved oxygen in thermally conditioned water to skin tissue of the appendage. Water is a well-known and often used penetration enhancer and easily penetrates into the stratum corium. Oxygen is easily dissolved into water but will not stay suspended for long periods of time. Recently it has been discovered that nano sized oxygen bubbles can also be easily suspended in water with the added benefit that the oxygen content of nano sized oxygen bubbles in water is greatly enhanced, additionally the properties of nano sized bubbles are charged having a negatively charged exterior and the buoyancy is also greatly reduced, therefore time that nano sized oxygen bubbles are suspended in the water can be months instead of hours. Therefore, water saturated with nano sizes oxygen bubbles and one or more water compatible penetration enhancers and utilized as an aqueous pressure distribution medium component of the compression exertion device would be highly beneficial and advantageous in supplying oxygen to peripheral nerves and tissues in the epidermal and dermis skin layers. In one or more embodiments, the thermally conditioned water including the nano sized oxygen bubbles and can be replaced between instances of blood supply occluding compression. Such replacement will allow replenishment of oxygen available for diffusion through the stratum corium and into the dermis skin layer.

Figure 2:
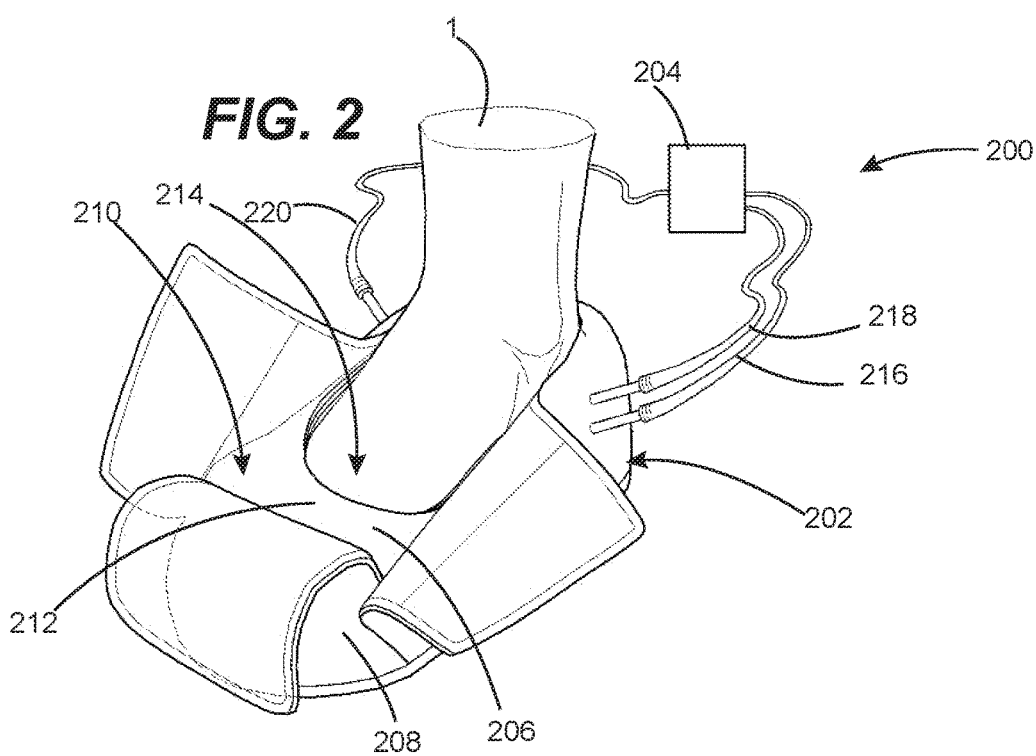
FIG. 2 is an illustrative view showing a compression exertion system configured in accordance with one or more embodiments of the present invention.

FIG. 2 shows a compression exertion system 200 configured in accordance with one or more embodiments of the present invention. The compression exertion system 200 includes a compression exertion device 202 operably connected to a pressure controller 204. The compression exertion device 202 and the pressure controller 204 are jointly configured for enabling pressurization of a compression-inducing medium within an expansion cavity of the compression exertion device. A wall of the expansion cavity can at least partially define an interior space of the compression exertion device and serve as an electrode for electrical communication through the appendage 1. The pressure controller 204 carries out system-managed pressurization of a compression-inducing medium within an expansion cavity of the compression exertion device 202 (e.g., via pressurized delivery of the compression-inducing medium) for causing blood supply occluding compression of an appendage 1 disposed within the compression exertion device 202. In one of more embodiments, the pressure controller 204 includes a programmable controlled pressure source that is fluidly interconnected to the compression exertion device 202 for enabling the pressure controller to carry out the system-managed pressurization of a compression-inducing medium within an expansion cavity of the compression exertion device 202 in the manner set forth above in reference to the method 100 discussed above.

Figure 3:
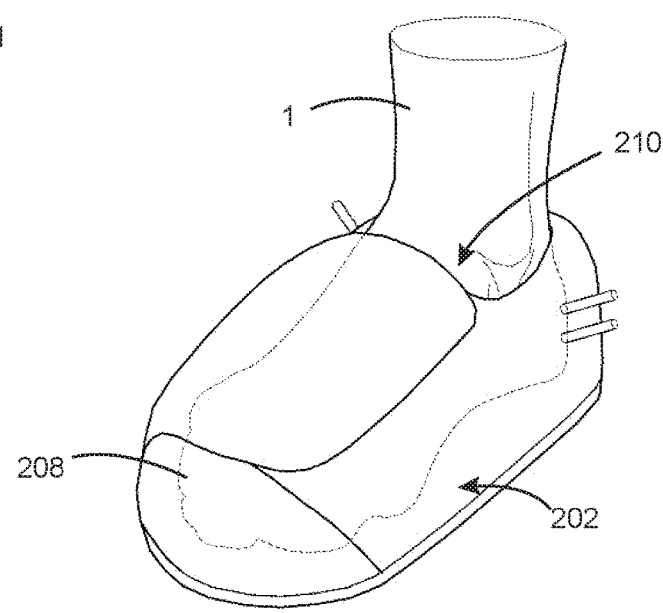
FIG. 3 is an illustrative view showing a compression exertion device in accordance with an embodiment of the present invention.

Referring to FIGS. 2-4, the compression exertion device 202 can include a compression body 206 and an outer body 208. The compression body 206 is fluidly interconnected with the pressure controller 204. Such fluid interconnection enables communication of a compression-inducing medium between the pressure controller 204 and the compression body 206 for causing the aforementioned blood supply occluding compression of the appendage 1 disposed within the compression exertion device 202.

The outer body 208 has an interior space 210 within the which the compression body 206 is located. The outer body 208 can serve to protect the compression body 206 from damage by physical contact with external items and to constrain expansion of an exterior surface 212 of the compression body 206 during application of blood supply occluding compression of the appendage 1. To this end, the outer body 208 can include one or more securement components (e.g., securable flaps) for allowing the compression body 206 to be fixedly disposed within the interior space 210 of the outer body 208. To constrain expansion of the exterior surface 212 of the compression body 206 during application of blood supply occluding compression of the appendage 1, the body 208 can be made from materials exhibiting limited or no deformation, expansion and/or elongation to thereby allow the outer body 208 to serve as an expansion limiting impediment relative to the compression body 206 when the compression body 206 is subject to pressurization by delivery of the compression-inducing medium via the pressure controller 204. One example of such a material is Cordura brand nylon.

The compression body 206 includes an interior space 214 adapted for having an appendage of a patient engaged therein. In one or more embodiments, the interior space 214 of the compression body 206 can be configured for having a foot engaged therein (e.g., a boot, shoe or slipper). In one or more other embodiments, the interior space 206 of the compression body 206 can be configured for having a hand engaged therein (e.g., a glove or mitten). The pressure controller 204 is fluidly and operably connected to the compression body 206 through one or more fluid transfer conduits 216, 218, 220. Each of the fluid transfer conduits 208, 210, 212 can be tubing or other elongated conveyance structure through which a gaseous and/or liquid (i.e., fluid) compression-inducing medium can flow for enabling the compression exertion device 202 to provide distributed pressure onto the appendage 1 for exerting blood supply occluding compression. Each of the fluid transfer conduits 216, 218, 220 can provide for flow of compression-inducing medium to the compression body 206, flow of compression-inducing medium from the compression body 206, ventilation of fluid from the compression body 206, or a combination thereof.

Figure 5:
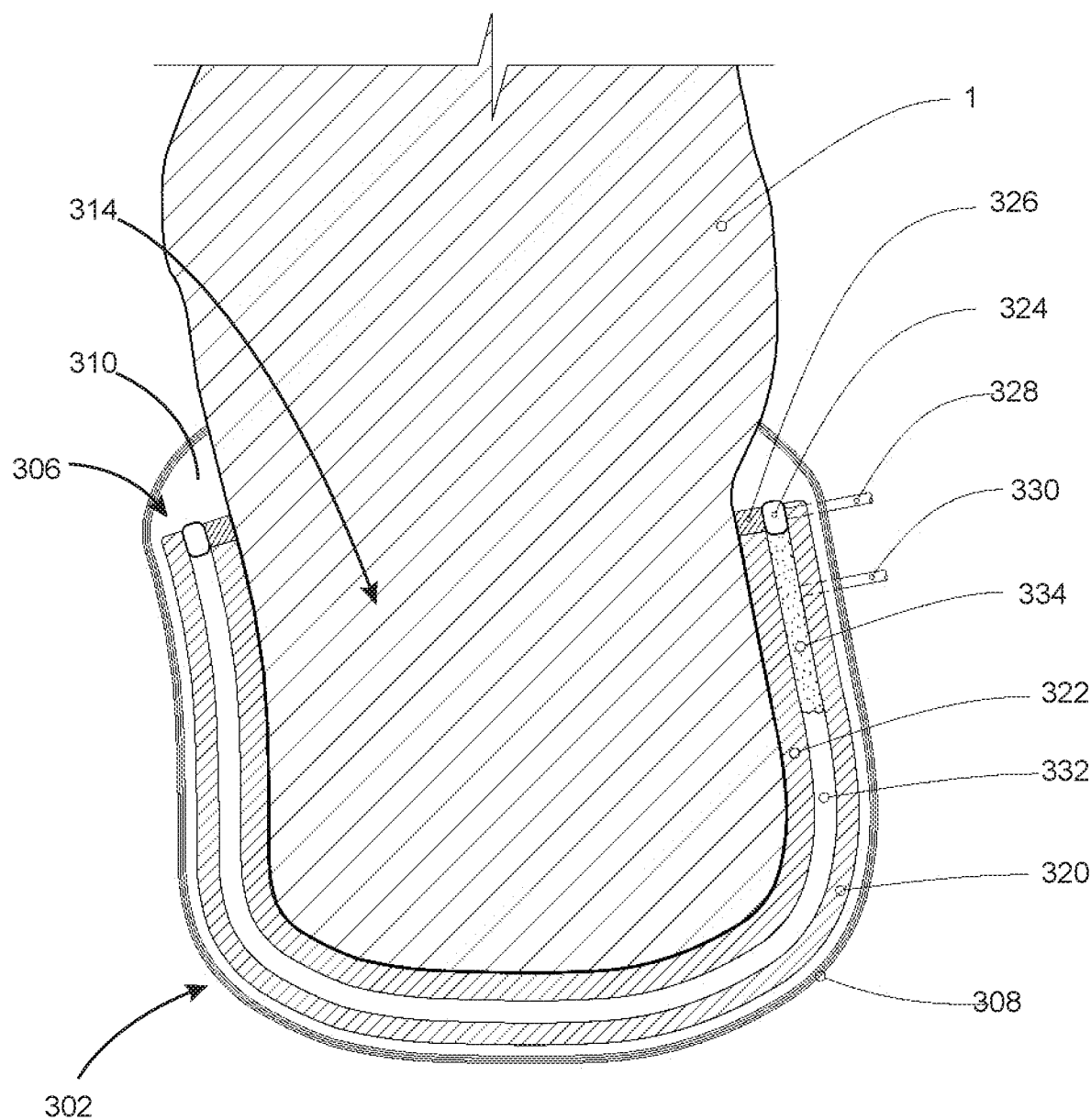
FIG. 5 is a cross-sectional view showing a first construction of a compression exertion device in accordance with one or more embodiments of the present invention.

Referring now to FIG. 5, a first construction of a compression exertion device in accordance with one or more embodiments of the present invention (i.e., compression exertion device 302) is shown, which can be used as a compression exertion device discussed above in reference to FIGS. 1-4. The compression exertion device 302 includes a compression body 306 and an outer body 308. The outer body 308 has an interior space 310 within the which the compression body 306 is located. The outer body 308 can serve to protect the compression body 306 from damage by physical contact with external items and to constrain expansion of the compression body 306 during application of blood supply occluding compression of an appendage 1 within an interior space 314 of the compression body 306.

The compression body 306 includes an outer enclosure 320, a pressure distribution article 322, a compression sealing bladder 324, a sealing component 326, a bladder connector 328 and an expansion cavity connector 330. The outer enclosure 320, the pressure distribution article 322, the compression sealing bladder 324 and the sealing component 326 jointly define an expansion cavity 332. A wall of the expansion cavity can at least partially define an interior space of the compression exertion device and serve as an electrode for electrical communication through the appendage 1. A compression-inducing medium 334 can be delivered into the expansion cavity 332 through the expansion cavity connector 330 for enabling the compression exertion device 302 to provide distributed pressure onto the appendage 1 for exerting blood supply occluding compression thereon. Such blood supply occluding compression is exerted on the appendage 1 directly by the pressure distribution article 322 under pressure provided by the compression-inducing medium 334 within the expansion cavity 332. The compression sealing bladder 324 can be inflated by a fluid disposed therein through the bladder connector 328, thereby sealing the sealing component 326 against an exterior surface of the appendage 1 to inhibiting flow of pressure distribution medium 334 from within a space jointly defined by the exterior surface of the appendage 1, the sealing component 326 and the outer enclosure 320. Inflation of the compression sealing bladder 324 may also cause the compression sealing bladder 324 to become engaged with the outer body 308. Optionally, the compression sealing bladder 324 may be bonded to the outer body 308.

It is disclosed herein that the pressure distribution article 322 is preferably formed from a material having properties enabling it to be conformed to a surface contour of the appendage 1. The pressure distribution article 322 preferably has a thickness and hardness that enables pressure within the expansion cavity 332 to be uniformly distributed onto the exterior surface of the appendage 1. To this end, in one or more embodiments, the pressure distribution article 322 is comprised of a moldable, substantially supple material conforming under pressure to irregular surface features of the appendage 1. One specific example of such a moldable, substantially supple material is anon-hardening moldable putty fitted about irregular surface features of the appendage 1. Another specific example of such a moldable, substantially supple material is a two-part reactant liquid rubber molded to conform about irregular surface features of the appendage 1.

In one or more embodiments, the material from which the pressure distribution article 322 is made is a polymeric or elastomeric material having a Shore hardness on the 00 scale of from about 0 to about 90, and more preferably from between about 0 and about 40 and still more preferably from between about 40 and about 80. The polymeric or elastomeric material can be of a material composition comprising any number of resilient materials compositions such as, by way of example, polysulfide, silicon, latex, polyurethane, polysulfide, and urethane.

The pressure distribution article 322 may be configured to provide for oxygen diffusion into tissue of the appendage 1. To this end, in one or more embodiments, the pressure distribution article 322 may include an open pore structure extending throughout. The open pore structure may be loaded with an oxygen carrying medium comprising a paste, cream, gel, serum, fluid or the like. In use, pressure exerted on the pressure distribution article 332 (e.g., by the compression-inducing medium 334) may compress the pressure distribution article 332 and cause dispersion of the oxygen carrying medium out of the open porous structures and onto the surface area of the epidermal skin. In this regard, oxygen from the oxygen carrying medium is thereby diffused through the stratum corium into the dermis skin layer and thereby diffused oxygen is supplied to the peripheral nerves and tissues of the dermis skin layer.

Figure 6:
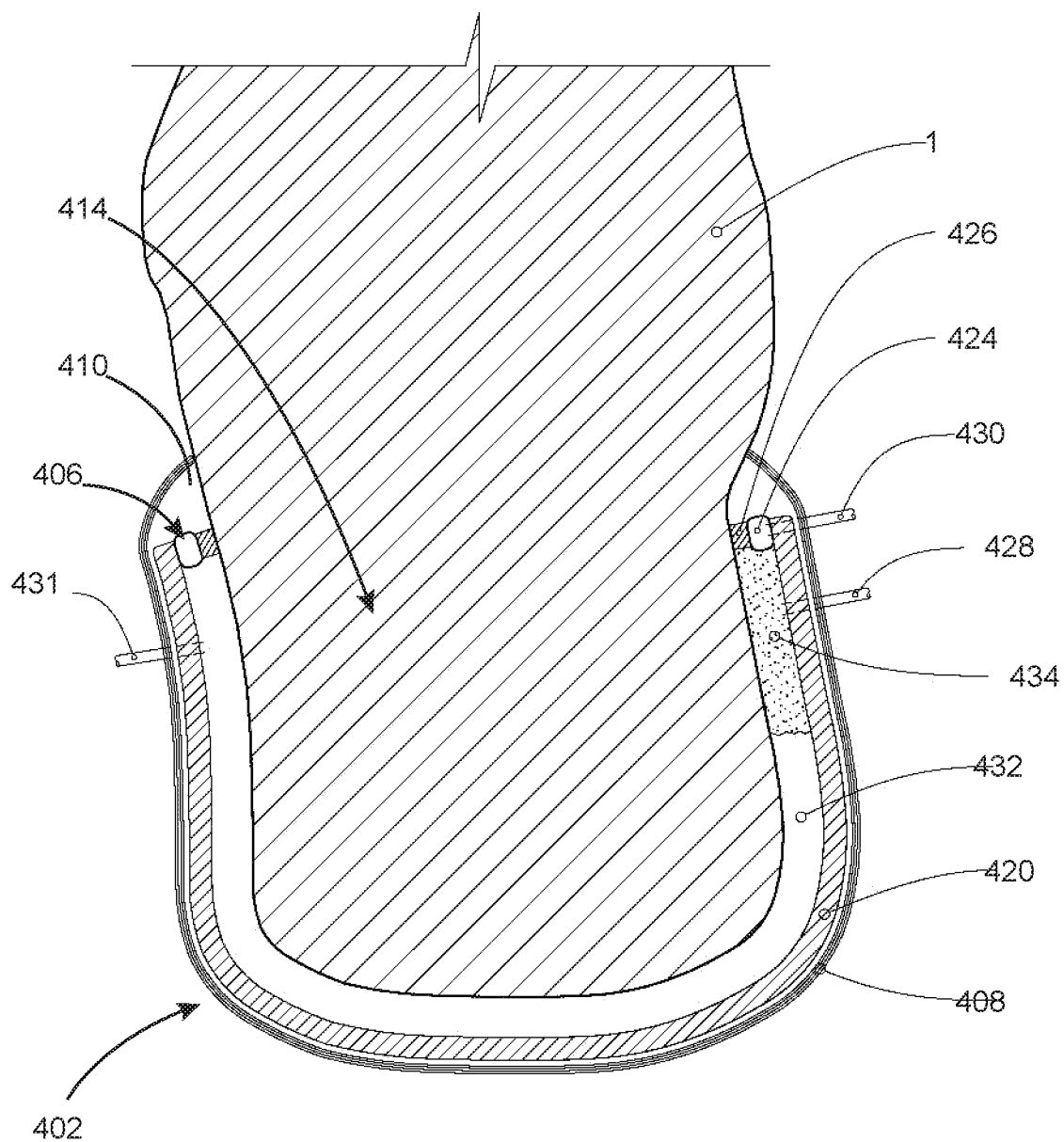
FIG. 6 is a cross-sectional view showing a second construction of a compression exertion device in accordance with one or more embodiments of the present invention.

Referring now to FIG. 6, a second construction of a compression exertion device in accordance with one or more embodiments of the present invention (i.e., compression exertion device 402) is shown, which can be used as a compression exertion device discussed above in reference to FIGS. 1-4. The compression exertion device 402 includes a compression body 406 and an outer body 408. The outer body 408 has an interior space 410 within the which the compression body 406 is located. The outer body 408 can serve to protect the compression body 406 from damage by physical contact with external items and to constrain expansion of the compression body 406 during application of blood supply occluding compression of an appendage 1 within an interior space 314 of the compression body 406.

The compression body 406 includes an outer enclosure 420, a compression sealing bladder 424, a sealing component 426, a bladder connector 428, an expansion cavity connector 430 and a vent connector 431. The appendage 1, the outer enclosure 420, the compression sealing bladder 424 and the sealing component 426 jointly define an expansion cavity 432. A wall of the expansion cavity can at least partially define an interior space of the compression exertion device and serve as an electrode for electrical communication through the appendage 1. A compression-inducing medium 434 can be delivered into the expansion cavity 432 through the expansion cavity connector 430 for enabling the compression exertion device 402 to provide distributed pressure onto the appendage 1 for exerting blood supply occluding compression thereon. Such blood supply occluding compression is exerted on the appendage 1 directly by the compression-inducing medium 434. The compression sealing bladder 424 can be inflated by a fluid disposed therein through the bladder connector 428, thereby sealing the sealing component 426 against an exterior surface of the appendage 1 to inhibiting flow or movement of compression-inducing medium 434 from within the expansion cavity 432. Inflation of the compression sealing bladder 424 may also cause the compression sealing bladder 424 to become engaged with the outer body 408. Optionally, the compression sealing bladder 424 may be bonded to the outer body 408 and the sealing component 426 bonded to the compression sealing bladder 424.

The compression-inducing medium 434 may be an aqueous oxygen carrying medium. In this regard, the compression-inducing medium 434 can be configured to provide for oxygen diffusion into tissue of the appendage 1 carried within the aqueous oxygen carrying medium into tissues of the appendage. In use, pressurization of the compression-inducing medium 434 causes intimate engagement of the compression-inducing medium 434 to enable such oxygen diffusion diffused through the stratum corium into the dermis skin layer and thereby diffused oxygen is supplied to the peripheral nerves and tissues of the dermis skin layer.

Figure 7:
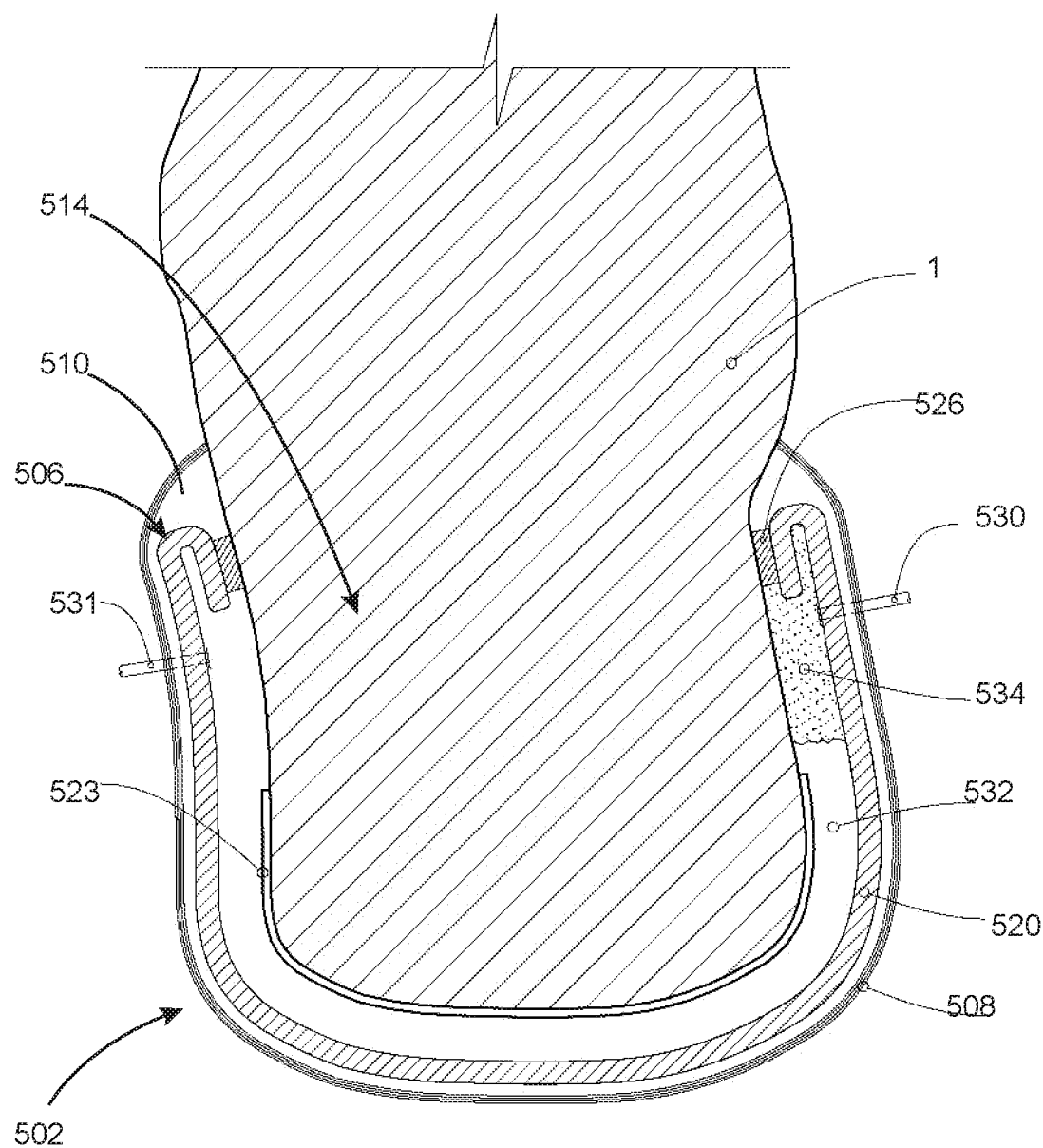
FIG. 7 is a cross-sectional view showing a third construction of a compression exertion device in accordance with one or more embodiments of the present invention

Referring now to FIG. 7, a third construction of a compression exertion device in accordance with one or more embodiments of the present invention (i.e., compression exertion device 502) is shown, which can be used as a compression exertion device discussed above in reference to FIGS. 1-4. The compression exertion device 502 includes a compression body 506 and an outer body 508. The outer body 508 has an interior space 510 within the which the compression body 506 is located. The outer body 508 can serve to protect the compression body 506 from damage by physical contact with external items and to constrain expansion of the compression body 506 during application of blood supply occluding compression of an appendage 1 within an interior space 514 of the compression body 506.

The compression body 506 includes an outer enclosure 520, stratum corium piercing structure 523, a sealing component 526, an expansion cavity connector 530 and a vent connector 531. The appendage 1 and the outer enclosure 520 jointly define an expansion cavity 532. A wall of the expansion cavity can at least partially define an interior space of the compression exertion device and serve as an electrode for electrical communication through the appendage 1. The outer enclosure 520 includes a perimeter edge portion 533 configured in a 'U-shaped manner' to enable pressurization of compression-inducing medium 534 delivered into the expansion cavity 532 through the expansion cavity connector 530 to create a sealing structure between the outer enclosure 520 and the sealing component 526, with the sealing component 526 providing a seal with the appendage 1. Such delivery of the compression-inducing medium 534 into the expansion cavity 532 also enables the compression exertion device 302 to provide distributed pressure onto the appendage 1 for exerting blood supply occluding compression thereon. Such blood supply occluding compression is exerted on the appendage 1 directly by the compression-inducing medium 534.

The compression-inducing medium 534 may be an aqueous oxygen carrying medium. In this regard, the compression-inducing medium 534 can be configured to provide for oxygen diffusion into tissue of the appendage 1 carried within the aqueous oxygen carrying medium into tissues of the appendage. In use, pressurization of the compression-inducing medium 534 causes intimate engagement of the compression-inducing medium 534 to enable such oxygen diffusion to be diffused through the stratum corium into the dermis skin layer and thereby diffused oxygen is supplied to the peripheral nerves and tissues of the dermis skin layer. To promote oxygen diffusion, pressurization of compression-inducing medium 534 delivered into the expansion cavity 532 having a stratum corium piercing structure 523 fixed to the epidermal skin portion of an appendage can be structured to permit diffusion of oxygen therethrough. To this end, the compression-inducing medium 534 may be an aqueous oxygen carrying medium. In this regard, the compression-inducing medium 534 can be configured to provide for oxygen diffusion into tissue of the appendage 1. In use, pressurization of the compression-inducing medium 534 causes intimate engagement of the compression-inducing medium 534 to enable such oxygen diffusion diffused through the stratum corium (e.g., including through one or more passages through the stratum corium piercing structure 523) into the dermis skin layer and thereby diffused oxygen is supplied to the peripheral nerves and tissues of the dermis skin layer. In one or more embodiments, the stratum corium piercing micro punctures may be pre-formed prior to insertion of an appendage without the piercing device being attached to the epidermal skin). A wall of the expansion cavity can at least partially define an interior space of the compression exertion device and serve as an electrode for electrical communication through the appendage 1.

Figure 8:
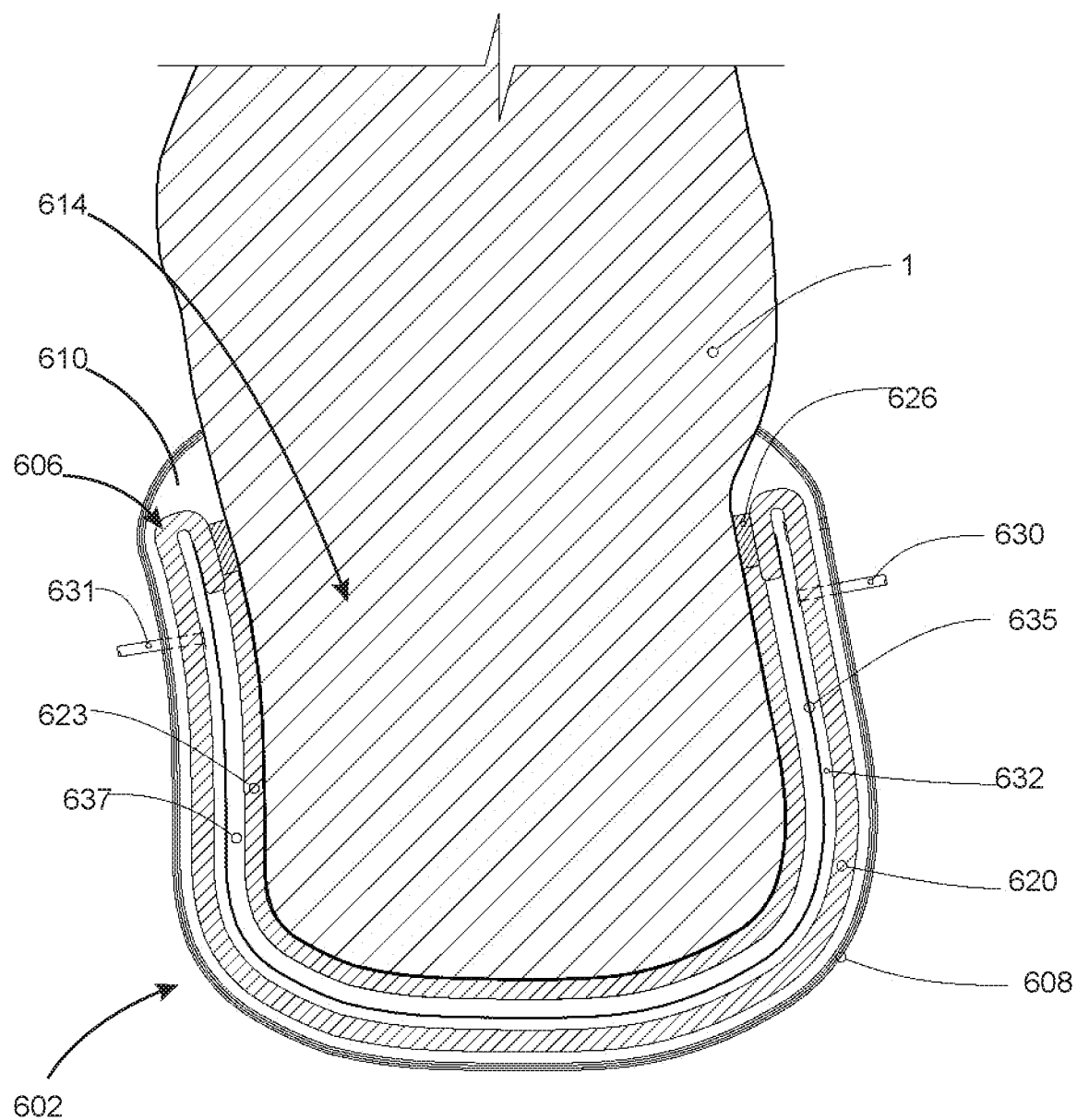
FIG. 8 is a cross-sectional view showing a fourth construction of a compression exertion device in accordance with one or more embodiments of the present invention.

Referring now to FIG. 8, a fourth construction of a compression exertion device in accordance with one or more embodiments of the present invention (i.e., compression exertion device 602) is shown, which can be used as a compression exertion device discussed above in reference to FIGS. 1-4. The compression exertion device 602 includes a compression body 606 and an outer body 608. The outer body 608 has an interior space 610 within the which the compression body 606 is located. The outer body 608 can serve to protect the compression body 606 from damage by physical contact with external items and to constrain expansion of the compression body 606 during application of blood supply occluding compression of an appendage 1 within an interior space 614 of the compression body 606.

The compression body 606 includes an outer enclosure 620, a pressure distribution article 622, a sealing component 626, a first expansion cavity connector 630, a second expansion cavity connector 631 and a cavity partition 635. The outer enclosure 620 includes a perimeter edge portion 633 configured in a 'U-shaped manner' to enable pressurization of compression-inducing medium delivered into the expansion cavity 632 through the first expansion cavity connector 630 to create a sealing structure between the outer enclosure 620 and the sealing component 626, with the sealing component 626 providing a seal with the appendage 1. A wall of the expansion cavity can at least partially define an interior space of the compression exertion device and serve as an electrode for electrical communication through the appendage 1. The outer enclosure 620 and the cavity partition 635 jointly define an expansion cavity 632. The pressure distribution article 623 and the cavity partition 635 jointly define an oxygen-carrying medium cavity 637. An oxygen-carrying medium can be provided in the oxygen-carrying medium cavity 637, with the pressure distribution article 622 being configured for enabling passage of oxygen from the oxygen-carrying medium through the pressure distribution article 622 for diffusion into tissue of the appendage 1 that is engaged with the pressure distribution article 622. A cavity partition in accordance with embodiments of the present invention can have passages for allowing transmission of the compression-inducing medium therethrough, be a membrane enabling transmission of oxygen of a compression-inducing medium therethrough, or a combination thereof.

Figure 9:
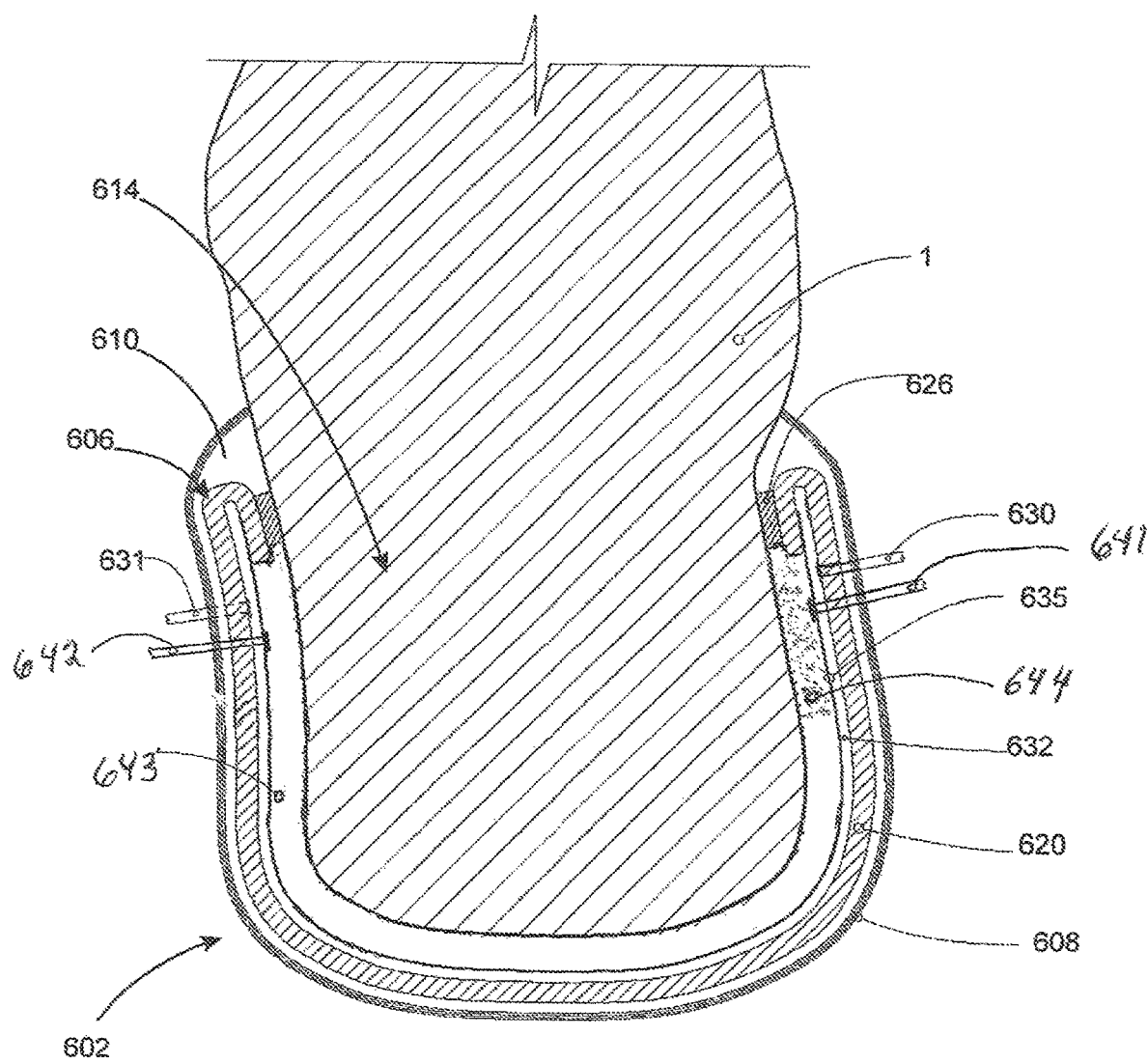
FIG. 9 is a cross-sectional view showing a fifth construction of a compression exertion device in accordance with one or more embodiments of the present invention.

As shown in FIG. 9, in one or more other embodiments, the compression exertion device 602 is provided with at least two expansion cavities for providing two separate pressure-inducing mediums, i.e., a first pressure inducing medium within the first expansion cavity 632 and a second pressure inducing medium within the oxygen-carrying medium cavity 637 (i.e., a second expansion cavity). The compression exertion device 602 can further include a third first expansion cavity connector 641 and a fourth expansion cavity connector 642. The outer enclosure 620 and the cavity partition 635 jointly define the expansion cavity 632. A wall of the expansion cavity can at least partially define an interior space of the compression exertion device and serve as an electrode for electrical communication through the appendage 1. The cavity partition 635 and a surface of the appendage 1 jointly define the oxygen-carrying medium cavity 637 (i.e., the second expansion cavity). In this respect, different pressure-inducing mediums and associated delivery pressures can be used for exerting blood supply occluding compression on the appendage 1 and for delivering oxygen (e.g., bio-available dissolved oxygen or nano oxygen bubble water solution) to the appendage via its epidermal skin layer.

A pressure distribution medium comprised of a bio-available dissolved oxygen or nano oxygen bubbles in an aqueous solution can be introduced through the first expansion cavity connector 630 into the first 632 and pressurized to a first pressure of, for example, from between about 10 mm hg and 25 mm hg for the duration of the chemotherapy treatment. The first pressure preferably provides a minimal pressure for displacing blood from the uppermost portion of the dermis skin layer. A compression inducing medium of air, gas or liquid can be introduced into the second expansion cavity 637 through the third expansion cavity connector 641 and is pressurized, for example, from between about 10 mm hg and 50 mm hg for a predetermined time preferable, for example, from between about 3 and 10 minutes, and more preferable from between about 10 and 30 minutes and still more preferably from between about 30 and 60 minutes and even more preferably from between about 60 to 120 minutes.

The pressure within the second expansion cavity 637 is cycled from a high pressurized state to a non-pressurized state. During the pressurized state, pressure within the second expansion cavity 637 expands the cavity partition 635 between the first and second expansion cavities 632, 637, thereby increasing the pressure impinged on the epidermal skin layer through the pressure distribution medium containing bio-available dissolved oxygen or nano oxygen bubbles in an aqueous solution, equal to the pressure within the second expansion cavity. During the non-pressurized cycle of the second expansion cavity 637, the pressure impinged on the first expansion cavity 632 from the second expansion cavity 637 can be reduced to atmospheric pressure and the pressure within the first expansion cavity 632 decreases and remains equal to the pressure applied within the first expansion cavity 632 prior to application of the higher impingement pressure in the second expansion cavity 637. In this manner, a minimal pressure is applied to the epidermal skin layer providing at least partial blood displacement from the dermis shin layer throughout the duration of the chemotherapy treatment.

In one or more embodiments, the same underlying treatment approach described above for the first and second expansion cavities 632, 637 can be practiced with a single expansion cavity. In such one or more embodiments, the second expansion cavity 637 has bio-available oxygen pressure distribution medium delivered thereto with a controllable pressure source. The pressures can be cycled from a minimal pressure state and then increased to the high-pressure state with the use of programmable precision controlled medical pumps, provided by numerous medical device manufactures.

Figure 10:
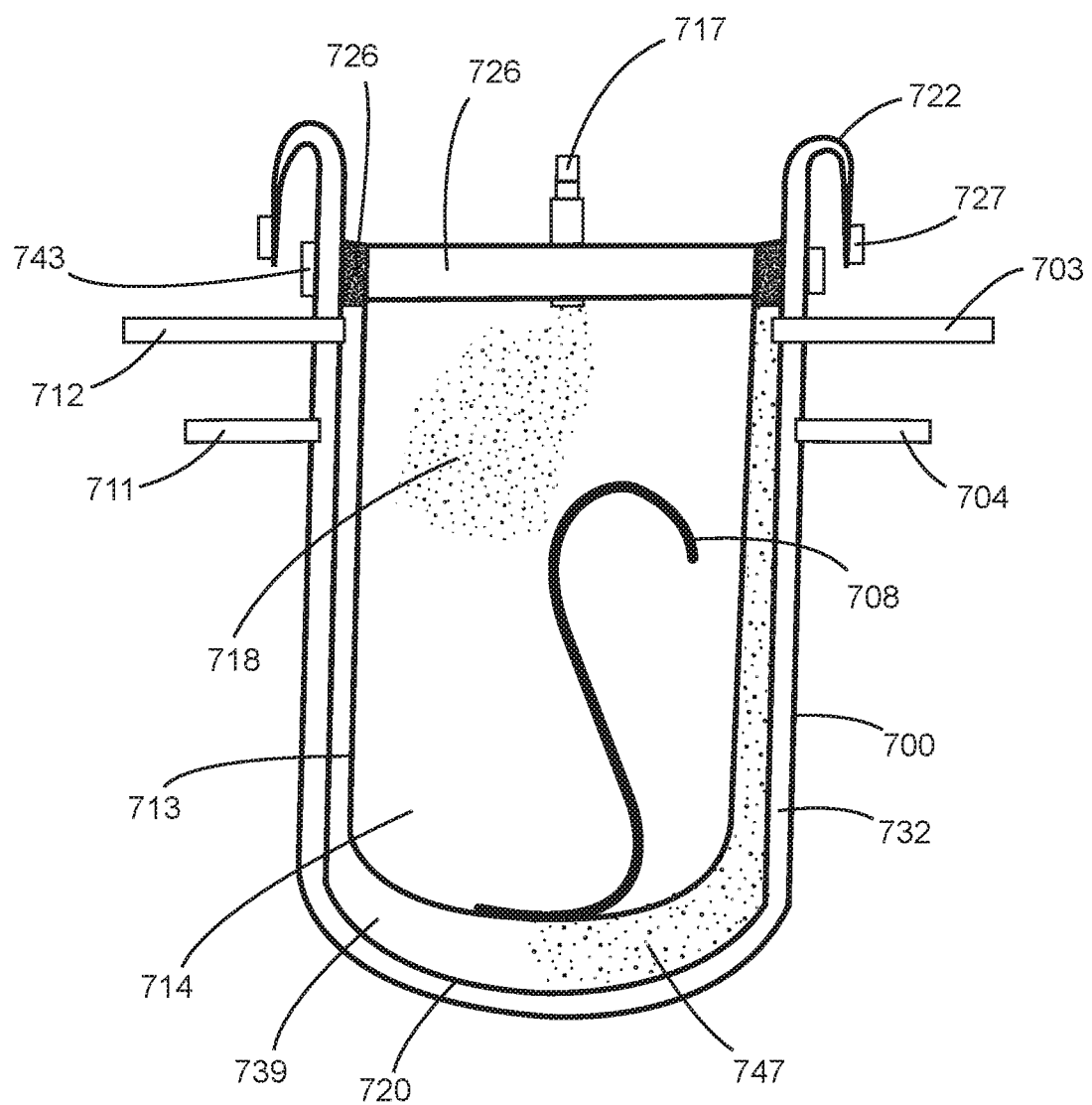
FIG. 10 is a cross-sectional view showing a sixth construction of a compression exertion device in accordance with one or more embodiments of the present invention.

Referring to FIG. 10, in one or more embodiments, a fifth construction of a compression exertion device in accordance with one or more embodiments of the present invention (i.e., compression exertion device 702) is shown, which can be used as a compression exertion device discussed above in reference to FIGS. 1-4. The compression exertion device 702 includes an outer body 708 that can also serve as a compression body of the compression exertion device 702. The compression exertion device 702 can be provided prepackaged in kit form that includes a pressure distribution medium 747 (e.g., a bioavailable oxygen pressure distribution medium) metered onto an interior surface of the outer body 708, whereby the pressure distribution medium 747 is package sealed within an interior space 714 of the compression exertion device 702. Where the pressure distribution medium 747 is a bioavailable oxygen pressure distribution medium, a removable packaging substrate 713 such as, for example, made of either one of a impervious film, foil, cellophane, plastic and the like is provided over an exposed surface of the pressure distribution medium 747 to limit escape of oxygen from in the bioavailable oxygen pressure distribution medium. A removal member 719 (e.g., a cord, strap or the like) is attached to a lower extreme end portion of the removable packaging substrate 713 for easy removal of the packaging substrate 713. Alternatively, removal of the packaging substrate 713 can expose an oxygen gas pervious membrane on top of the pressure distribution medium 747 through which oxygen molecules can flow. The pressure distribution medium 747 defines a pressure distribution medium space 739 within the interior space 714 of the compression exertion device 702.

The compression exertion device 702 can include a gas-charging inlet connector 717 for charging the interior space 714 of the compression exertion device 702 with oxygen gas 718 once an appendage is located within the interior space 714 and a sealed interface is formed between the appendage and the compression exertion device 702 via a sealing component 726. The sealing component 726 can include, for example, a physical seal, a adhesive material seal or the like. Gaseous oxygen can be injected into the interior space 714 through the gas-charging inlet connector 717 and sealed therein under a predetermined pressure to minimize release of oxygen from the bio-available pressure distribution medium. Preferably, the outer body 708 can have a given thickness capable of resisting expansion up to about 3 psi. Expansion cavity connectors inlet 704 and outlet 711 provide for a connecting means to a pressure source to provide precise impingement pressure of a pressure medium within a first expansion cavity 732 after insertion of an appendage into the interior space 714 and sealing of the outer body 708 thereon. Expansion cavity connectors inlet 703 and outlet 712 provide for replacement and or replenishment of the pressure distribution medium 707 prior to or during commencement of the chemotherapy procedure.

An extension 722 of the joined outer body 708 and the cavity partition 720 may be folded over and down until the appendage is inserted into the compression exertion device 702 at that point in time the extension 722 is folded upward after a protection member (not shown) on the sealing component 726 is removed and sealed to the epidermal portion of the appendage after is located within the interior apace of the compression exertion device 702. The extension 722 may include an additional sealing component 727. In one or more embodiments, a strap 743 (e.g., hook and loop such as VELCRO) may be wrapped around and fastened to the outside portion of the extension 722 to help maintain seal between the extension 722 and the epidermal portion of the appendage during pressurization. The oxygen pressure distribution medium may be additionally supplied in the kit with a dispenser filled with the aqueous pressure distribution medium having a inter connectable means to the expansion cavity connector.

In one or more embodiments, the compression exertion device and parts thereof can be made from a variety of man-made or natural rubbers, plastics and the like, having a hardness on the harness scale 00 of from between 10 to 90 and resistance to expansion from between about 10 mm hg and 155 mm hg.

In one or more embodiments, the compression exertion device may comprise a membrane for passage of oxygen while other parts may comprise woven non-woven textile resistant to expansion.

In one or more embodiments, an aqueous bio-available oxygen pressure distribution medium comprises a solution of water, comprising nano bubbles (preferably smaller than 200 nm), a water solution comprising a mixture of at least one or more of water, urea, glycol, ethanol, taurine to name a few and nano oxygen bubbles therein providing thereby a safe epidermal penetrating aqueous oxygen carrier providing diffusion of oxygen into the epidermal skin layer and into the dermis skin layer and tissues therein, an oxygen charged perfluorocarbon composition.

In one or more embodiments, the pressure distribution medium is pressurized from between about 10 mm hg and 50 mm hg and is in intimate contact with the epidermal skin layer for the duration of the chemotherapy treatment without a cyclical operation.

In one or more embodiments, the aqueous pressure distribution medium is pressurized from between about 10 mm hg and 50 mm hg and is in intimate contact with the epidermal skin layer for the duration of the chemotherapy treatment without a cyclical operation.

As can be seen from the above disclosures, devices, systems and methods in accordance with one or more embodiments of the present invention are specifically adapted to provide intermittent displacement of blood to mitigate peripheral nerve neuropathy generally and chemotherapy-induced neuropathy more specifically. Such devices, systems and methods are configured to enable precise, uniform and controlled blood displacing compression of a patient's appendage (e.g., hand(s), foot(feet) and the like) This precise, uniform and controlled blood displacing compression is imparted upon the epidermal and dermis skin layers of a patient's appendage(s) to decrease the time that free nerve endings located in the epidermal and encapsulated nerve endings located in the dermis skin layers are exposed to nerve damaging chemotherapy chemicals. To further limit peripheral nerve neuropathy, in combination with the aforementioned controlled blood-occluding compression, devices, systems and methods in accordance with one or more embodiments of the present invention can be adapted to simultaneously provide an oxygen supply to the nerve endings through an aqueous oxygen containing medium (e.g., an oxygen containing pressure distribution medium). In this regard, embodiments of the present invention cause distributed compression that displaces and at least partially occludes the blood supply to the dermis and epidermal skin layer that are highly susceptible to the damage caused by chemotherapeutic agents while actively mitigating tissue damage resulting from blood-occluding compression thereof. Below are further disclosures directed to devices, systems and methods in accordance with one or more embodiments of the present invention.

In one or more embodiments, a compression exertion device is provided having an outer enclosure enclosing about at least a portion of the feet or hands (i.e., appendages). An expansion limiting impediment can be fixed and enclosed about the outer enclosure to limit the outward expansion of the outer enclosure. The outer enclosure can comprise an expansion cavity partition conforming to the inner surface of the outer enclosure and sealed about an opening in the outer enclosure for insertion of an appendage.

In one or more embodiments, a system is provided having a programmable controlled pressure source adapted to introduce a compression inducing medium (fluid or gas) in to an expansion cavity of a compression exertion device for achieving controlled intermittent inflation of the expansion cavity when the compression inducing medium is introduced and pressurized within the expansion cavity from the programmable controlled pressure source. The expansion cavity partition when pressurized, inflates and expands towards the epidermal skin portion of an appendage inserted within the opening of the outer enclosure, expanding away from the inside surface of the outer enclosure to the direction of the epidermal skin surface, adjacent to the inside surface of the expansion cavity partition. The pressure distribution article is of a flexible form fitting material contoured to the irregular surface features of the feet and hands and the inside portion of the expansion cavity partition. The expansion cavity partition when controllably inflated with a gas or liquid will cause a timed, temperature controlled and regulated pressure to be impinged upon the pressure distribution medium article and cause substantially uniform compression of the irregular surface features of at least a portion of the epidermal skin layer of the appendage, displacing blood within the dermis skin layers and one of at least partially occluding or complete occlusion of capillary blood vessels supplying blood to the nerve endings within the dermis skin layer, and thereby at least partially occludes capillary blood vessels supplying blood to the nerve endings in the dermis skin layer, until a predetermined time of blood displacement and capillary blood vessel occlusion has passed. The cycle of compression begins prior to commencement of the chemotherapy treatment. After a predetermined time of compression, the programmable controlled pressure source device can return pressure within the expansion cavity from between the 50 mm hg and 25 mm hg high pressure to atmospheric pressure for a predetermined time, allowing blood oxygen supply to the dermis skin layers, preventing damage to skin tissues and nerve endings for lack of blood oxygen supply. Blood is allowed to circulate for a predetermined time to replenish human tissue with oxygen and the cycle is then repeated as needed.

In one or more embodiments, a self-contouring pressure distribution article (e.g., flowable or non-flowable medium) comprising a gas or liquid is provided for uniformly compressing irregular surface features of at least a portion of the appendage(s). Additionally, the self-contouring pressure distribution medium can be formulated to comprise an oxygen enriched air or liquid, fluid, gel, cream, serum, paste and provides simultaneous epidermal and dermis skin compression and facilitates diffusion of oxygen into at least portion of epidermal and dermis skin tissues of the appendage(s) during compression and displacement of blood within the dermis skin layer of the appendage. The self-contouring pressure distribution medium being in contact with the epidermal skin portion of at least a portion of the appendage(s) results in oxygen being diffused through the epidermal skin layer.

In one or more embodiments, an expansion limiting impediment can be fixed and bound about the outer enclosure to impede outward expansion of the outer enclosure.

In one or more embodiments, a flexible expansion cavity partition can be fixed and sealed to form an expansion cavity, whereby the expansion cavity partition expands toward an exterior surface of the appendage during pressurization of the compression-inducing medium by an interconnected programmable controlled pressure source into the expansion cavity, thereby expanding the expansion cavity partition toward the appendage and thereby pressure is impinged upon the pressure distribution article and/or the self-contouring pressure distribution medium to uniformly compress irregular epidermal surface features of the appendage(s).

In one or more embodiments, one or more penetration enhancers within an aqueous bio-available oxygen solution can be utilized to modify the stratum corium prior to or in combination with the components of the self-contouring pressure distribution medium of the present invention. The compression of the epidermal and dermis skin layers with the self-contouring pressure distribution medium can comprise an oxygen carrier that includes at least one of a penetration enhancer, one or more oxygen charged perfluorocarbon compositions with preference to a perfluorodecalin, one or more pharmaceutical grade emulsifiers, one or more surfactants, water formulated into a fluid, gel, serum, cream or the like. Formulations of fluorocarbon oxygen carriers, surfactants, emulsions and penetration enhancers facilitates oxygen diffusion into and through the stratum corium into the dermis skin layer, thereby causing diffusion of oxygen supply to peripheral nerve endings and skin tissue during the time blood is being displaced and at least partially occluded from the dermis skin layer.

In one or more embodiments, the self-contouring pressure distribution medium can comprise nano sized oxygen bubbles in thermally conditioned water and is replaced between cycles of compression and decompression of the self-contouring pressure distribution medium (e.g., the compression-inducing medium) thereby displacing from within the outer enclosure previously utilized thermally conditioned water comprising nano sized dissolved oxygen (i.e., a self-contouring pressure distribution medium) and replacing with fresh thermally conditioned water comprising nano-sized dissolved oxygen to thereby maintain high levels of oxygen available for diffusion through the stratum corium and into the dermis skin layer.

In one or more embodiments, a sealing component of a compression exertion device is provided for sealing between the outer enclosure and the epidermal skin surface of an appendage, where the sealing component can be an applied adhesive, a dual sided adhesive tape, a tacky compressible rubber or the like.

In one or more embodiments, the compression exertion device is provided with at least one of a pressure sensor and a blood oxygen sensor in functional contact with the appendage for enabling monitoring of pressure exerted on the appendage and a blood oxygen level within the appendage and enable adjustment of system parameters to affect such pressure and/or blood oxygen level.

In one or more embodiments, a pressure exertion device may be fitted with an negative electrode portion of an iontophoresis device and connecting means within the compression cavity adjacent to the epidermal shin of the appendage. The negative electrode can be shaped to match an inside portion of the pressure excretion device. The negative electrode of the iontophoresis device can be covered with a pressure distribution medium solution of nano oxygen bubble water that is premixed with water compatible penetration enhancers, nano bubble stabilizers such as anionic surfactants and minerals to slightly increase the alkalinity of the aqueous pressure distribution solution. The nano oxygen bubbles are negatively charged and saturated throughout the pressure distribution medium. A positive electrode can be attached to a portion of the appendage away from the pressure exertion devise. The negative electrode can repel the negatively charged nano oxygen bubbles away from the negative electrode and pushes the nano oxygen bubbles into the epidermal skin layer being pushed by the negative electrical force and attracted by the positive electrical force of the positive electrode as current and voltage are applied to the electrodes and thereby provides oxygen diffusion to tissues and nerves within the epidermal and dermis skin layers during the pressure cycle of the pressure excursion device.

Although the invention has been described with reference to several exemplary embodiments, it is understood that the words that have been used are words of description and illustration, rather than words of limitation. Changes may be made within the purview of the appended claims, as presently stated and as amended, without departing from the scope and spirit of the invention in all its aspects. Although the invention has been described with reference to particular means, materials and embodiments, the invention is not intended to be limited to the particulars disclosed; rather, the invention extends to all functionally equivalent technologies, structures, methods and uses such as are within the scope of the appended claims.

What is claimed is:

1. A method for mitigating peripheral nerve neuropathy associated with chemotherapy treatment, comprising:
    exerting a compressive pressure on a body part of a patient positioned within an interior space of a compression exertion device during administration of at least a portion of a prescribed amount of delivery of a chemotherapeutic agent to the patient, wherein the compressive pressure is exerted for causing at least one of a magnitude of the compressive pressure and a duration of time for said compressive pressure being exerted to at least one of occlude blood flow into dermis tissue of the body part and reduce blood flow into dermis tissue of the body part, wherein exerting the compressive pressure on the body part includes delivering a compression-inducing medium into at least one of the interior space of the compression exertion device and an expansion cavity of the compression exertion device; and
    communicating an electrical signal through the body part for causing forced-diffusion of an oxygen-carrying compression-inducing medium therethrough, wherein the oxygen-carrying compression-inducing medium provides negatively charged nano oxygen bubbles and wherein communicating the electrical signal comprises said electrical signal being provided to an electrode of the compression exertion device to cause the negatively charged nano oxygen bubbles to be repelled away from the electrode and to be pushed into the epidermis skin layer.

2. A method for mitigating peripheral nerve neuropathy associated with chemotherapy treatment, comprising:
    exerting a compressive pressure on a body part of a patient positioned within an interior space of a compression exertion device during administration of at least a portion of a prescribed amount of delivery of a chemotherapeutic agent to the patient, wherein the compressive pressure is exerted for causing at least one of a magnitude of the compressive pressure and a duration of time for said compressive pressure being exerted to at least one of occlude blood flow into dermis tissue of the body part and reduce blood flow into dermis tissue of the body part, wherein exerting the compressive pressure on the body part includes delivering a compression-inducing medium into at least one of the interior space of the compression exertion device and an expansion cavity of the compression exertion device having a wall at least partially defining the interior space, wherein delivering the compression-inducing medium includes delivering the compression-inducing medium into the interior space of the compression exertion device, wherein the compression-inducing medium is an oxygen-carrying medium capable of diffusing oxygen into at least one of the epidermis tissue and dermis tissue of the body part, and wherein exerting the compressive pressure on the body part includes:
        maintaining a current volume of the oxygen-carrying medium under pressure within the interior space of the compression exertion device for at least one of a first designated period of time and until a level of oxygen in the oxygen-carrying medium decreases below a prescribed threshold level;

removing at least a portion of the current volume of oxygen-carrying medium during said administering of the chemotherapeutic agent;

delivering a replacement volume of oxygen-carrying medium into the interior space of the compression exertion device after removing the at least a portion of the current volume of oxygen-carrying medium to create a new volume of the oxygen-carrying medium within the interior space of the compression exertion device; and pressurizing the new volume of oxygen-carrying medium to at least one of occlude blood flow into dermis tissue of the body part and reduce blood flow into dermis tissue of the body part.

3. A method for mitigating peripheral nerve neuropathy associated with chemotherapy treatment, comprising:

exerting a compressive pressure on a body part of a patient positioned within an interior space of a compression exertion device during administration of at least a portion of a prescribed amount of delivery of a chemotherapeutic agent to the patient, wherein the compressive pressure is exerted for causing at least one of a magnitude of the compressive pressure and a duration of time for said compressive pressure being exerted to at least one of occlude blood flow into dermis tissue of the body part and reduce blood flow into dermis tissue of the body part, wherein exerting the compressive pressure on the body part includes delivering a compression-inducing medium into at least one of the interior space of the compression exertion device and an expansion cavity of the compression exertion device having a wall at least partially defining the interior space, wherein delivering the compression-inducing medium includes delivering the compression-inducing medium into the interior space of the compression exertion device, wherein the compression-inducing medium is an oxygen-carrying medium capable of diffusing oxygen into the epidermal and dermis tissue of the body part, wherein the compression exertion device includes an expansion cavity at least partially surrounding the interior space of the compression exertion device, wherein exerting the compressive pressure on the body part of the patient during at least a portion of the prescribed amount of delivery includes causing pressurized delivery of the compression-inducing medium into the expansion cavity of the compression exertion device, and wherein exerting the compressive pressure is initiated prior to said administering of the chemotherapeutic agent and wherein administering the chemotherapeutic agent is initiated after blood flow into dermis tissue of the body part is at least one of occluded and reduced.

4. A method for mitigating peripheral nerve neuropathy associated with chemotherapy treatment, comprising:

exerting a compressive pressure on a body part of a patient positioned within an interior space of a compression exertion device during administration of at least a portion of a prescribed amount of delivery of a chemotherapeutic agent to the patient, wherein the compressive pressure is exerted for causing at least one of a magnitude of the compressive pressure and a duration of time for said compressive pressure being exerted to at least one of occlude blood flow into dermis tissue of the body part and reduce blood flow into dermis tissue of the body part, wherein exerting the compressive pressure on the body part includes delivering a compression-inducing medium into at least one of the interior space of the compression exertion device and an expansion cavity of the compression exertion device having a wall at least partially defining the interior space, wherein delivering the compression-inducing medium includes delivering the compression-inducing medium into the interior space of the compression exertion device, wherein the compression-inducing medium is an oxygen-carrying medium capable of diffusing oxygen into the epidermal and dermis tissue of the body part, wherein the compression exertion device includes an expansion cavity at least partially surrounding the interior space of the compression exertion device, wherein exerting the compressive pressure on the body part of the patient during at least a portion of the prescribed amount of delivery includes causing pressurized delivery of the compression-inducing medium into the expansion cavity of the compression exertion device, and;

releasing at least a portion of said compressive pressure after said administering of the chemotherapeutic agent is initiated; and reapplying said compressive pressure after blood flow is resumed through the body part for at least a designated duration of time.

5. A method for mitigating peripheral nerve neuropathy associated with chemotherapy treatment, comprising:

exerting a compressive pressure on a body part of a patient positioned within an interior space of a compression exertion device having an outer enclosure during administration of at least a portion of a prescribed amount of delivery of a chemotherapeutic agent to the patient, wherein the compressive pressure is exerted for causing at least one of a magnitude of the compressive pressure and a duration of time for said compressive pressure being exerted to at least one of occlude blood flow into dermis tissue of the body part and reduce blood flow into dermis tissue of the body part, wherein exerting the compressive pressure on the body part includes delivering a compression-inducing medium into at least one of the interior space of the compression exertion device and an expansion cavity of the compression exertion device having a wall at least partially defining the interior space, and wherein exerting the compressive pressure on the body part includes providing an expansion limiting impediment to impede outward expansion of the outer enclosure.

6. A method for mitigating peripheral nerve neuropathy associated with chemotherapy treatment, comprising:

exerting a compressive pressure on a body part of a patient positioned within an interior space of a compression exertion device during administration of at least a portion of a prescribed amount of delivery of a chemotherapeutic agent to the patient, wherein the compressive pressure is exerted for causing at least one of a magnitude of the compressive pressure and a duration of time for said compressive pressure being exerted to at least one of occlude blood flow into dermis tissue of the body part and reduce blood flow into dermis tissue of the body part, wherein exerting the compressive pressure on the body part includes delivering a compression-inducing medium into at least one of the interior space of the compression exertion device and an expansion cavity of the compression exertion device having a wall at least partially defining the interior space, and wherein exerting the compressive pressure on the body part includes exerting the compressive pressure using a sealing component of the pressure exertion device engageable with at least one of a portion of the body part and a limb to which the body part is attached when the body part is positioned within the interior space.

7. The method of claim 4, further comprising:
diffusing dissolved oxygen within an aqueous compression inducing medium into epidermis tissue of the body part;
wherein at least a portion of said diffusing and at least a portion of said exerting are performed simultaneously.

8. The method of claim 4, further comprising:
diffusing negatively charged nano oxygen bubbles within an aqueous compression inducing medium into epidermis tissue of the body part; and
wherein at least a portion of said diffusing and at least a portion of said exerting are performed simultaneously.

9. The method of claim 4 wherein:
exerting the compressive pressure is initiated prior to said administering of the chemotherapeutic agent; and
administering the chemotherapeutic agent is initiated after blood flow into dermis tissue of the body part is at least one of occluded and reduced.

10. The method of claim 9, further comprising:
releasing at least a portion of said compressive pressure after said administering of the chemotherapeutic agent is initiated; and
reapplying said compressive pressure after blood flow is resumed through the body part for a designated duration of time.

11. The method of claim 4 wherein exerting the compressive pressure on the body part includes pressurizing a compression-inducing medium surrounding the body part.

12. The method of claim 11 wherein the compression-inducing medium comprises a negatively-charged nano oxygen bubbles in an aqueous solution.

13. The method of claim 1, wherein:
a wall of the compression exertion device at least partially defines the interior space of the compression exertion device; and
the wall comprises the electrode.

14. The method of claim 1, further comprising:
prior to or in combination with the body part becoming positioned within the interior space of the compression excretion devise, altering one or more physical attribute of the stratum corium of the tissue of the body part for promoting transfer of gaseous and/or liquid material therethrough.

15. The method of claim 14 wherein:
said altering of the stratum corium includes soaking the body part in an aqueous solution of water comprising a penetration enhancer for a period of time prior to commencement of said exerting the compressive pressure to enable an oxygen flowable medium to deliver oxygen into the tissue of the body part; and
the penetrating enhancer comprises water having nano-sized oxygen bubbles therein.

16. The method of claim 14 wherein said altering one or more physical attribute of the stratum corium includes performing said altering using at least one of adhesive tape stripping, micro-punctures, micro dermal abrasions and chemical peels.

17. The method of claim 2 wherein:
the compression exertion device includes an expansion cavity at least partially surrounding the interior space of the compression exertion device; and
exerting the compressive pressure on the body part of the patient during at least a portion of the prescribed amount of delivery includes causing pressurized delivery of the compression-inducing medium into the expansion cavity of the compression exertion device.

18. The method of claim 4, further comprising:
prior to exerting the compressive pressure and administering the chemotherapeutic agent to the patient, providing in the interior space of the compression exertion device an initial volume of oxygen-carrying medium capable of diffusing oxygen into the epidermis tissue of the body part.

19. The method of claim 18 wherein said oxygen-carrying medium comprises negatively-charged, nano-sized oxygen bubbles.

20. The method of claim 18 wherein:
the initial volume of oxygen-carrying medium is a self-contouring pressure distribution article that uniformly applies compressive pressure onto irregular surfaces of the body part; and
delivering the compression-inducing medium into the expansion cavity of the compression exertion device causes a cavity partition defining the expansion cavity to exert compressive force on the initial volume of oxygen-carrying medium around substantially an entire surface area of the body part.

21. The method of claim 18 wherein exerting the compressive pressure on the body part includes:
maintaining the initial volume of the oxygen-carrying medium under pressure for at least one of a first designated period of time and until a level of oxygen in the initial volume of oxygen-carrying medium decreases below a prescribed threshold level;
removing at least a portion of the initial volume of oxygen-carrying medium during said administering of the chemotherapeutic agent;
delivering a replacement volume of oxygen-carrying medium into the interior space of the compression exertion device after removing the at least a portion of the initial volume of oxygen-carrying medium to create a new volume of the oxygen-carrying medium within the interior space of the compression exertion device; and
pressurizing the new volume of oxygen-carrying medium sufficient to at least one of occlude blood flow into dermis tissue of the body part and reduce blood flow into dermis tissue of the body part.

22. The method of claim 5 wherein exerting the compressive pressure on the body part includes cycling the compressive pressure between a first designated pressure and a second designated pressure higher than the first designated pressure.

23. The method of claim 5 wherein exerting the compressive pressure on the body part includes thermally conditioning the compression-inducing medium to a temperature-controlled and regulated pressure to be impinged upon the body part of the patient.

24. The method of claim 6 wherein exerting the compressive pressure on the body part is performed for exerting a designated amount of thermally conditioned, equally distributed and controlled blood displacing compression pressure on the body part.

25. The method of claim 6, wherein the compression-inducing medium comprises one or more oxygen charged perfluorocarbon compositions.

26. The method of claim 18 wherein exerting the compressive pressure on the body part includes thermally conditioning the compression-inducing medium to a temperature-controlled and regulated pressure to be impinged upon the body part.

27. The method of claim 6 wherein exerting the compressive pressure on the body part includes thermally conditioning the compression-inducing medium to a temperature-controlled and regulated pressure to be impinged upon the body part.

28. The method of claim 18 wherein exerting the compressive pressure on the body part is performed for exerting a designated amount of thermally conditioned, equally distributed and controlled blood displacing compression pressure on the body part.

29. The method of claim 5 wherein exerting the compressive pressure on the body part is performed for exerting a designated amount of thermally conditioned, equally distributed and controlled blood displacing compression pressure on the body part.

30. The method of claim 18 wherein the compression-inducing medium comprises one or more oxygen charged perfluorocarbon compositions.

31. The method of claim 5 wherein the compression-inducing medium comprises one or more oxygen charged perfluorocarbon compositions.

\* \* \* \* \*